(12) United States Patent
Sasayama et al.

(10) Patent No.: US 7,887,523 B2
(45) Date of Patent: Feb. 15, 2011

(54) DISPOSABLE DIAPER

(75) Inventors: Kenichi Sasayama, Kagawa (JP);
Hirotomo Mukai, Kawaga (JP);
Tomoko Tsuji, Kawaga (JP); Tatsuya Hashimoto, Kawaga (JP); Kei Wakasugi, Kawaga (JP)

(73) Assignee: Uni-Charm Corporation, Ehime (JP)

( * ) Notice: Subject to any disclaimer, the term of this patent is extended or adjusted under 35 U.S.C. 154(b) by 0 days.

(21) Appl. No.: 11/860,927

(22) Filed: Sep. 25, 2007

(65) Prior Publication Data

US 2008/0269711 A1    Oct. 30, 2008

(30) Foreign Application Priority Data

Sep. 27, 2006   (JP)  ............................... 2006-263365
Sep. 27, 2006   (JP)  ............................... 2006-263366
Sep. 27, 2006   (JP)  ............................... 2006-263367

(51) Int. Cl.
*A61F 13/15*      (2006.01)
*A61F 13/20*      (2006.01)

(52) U.S. Cl. ........................... 604/385.09; 604/385.01; 604/385.23; 604/385.24; 604/385.11

(58) Field of Classification Search ............ 604/385.09, 604/385.01, 385.23, 385.14, 385.24, 385.11
See application file for complete search history.

(56) References Cited

U.S. PATENT DOCUMENTS

| | | | | |
|---|---|---|---|---|
| 833,849 | A | * | 10/1906 | Schiff ........................... 604/396 |
| 1,751,832 | A | * | 3/1930 | Menzin ........................... 2/123 |
| 1,765,415 | A | * | 6/1930 | La Bombard et al. ........ 206/297 |
| 2,635,250 | A | * | 4/1953 | Williamson ..................... 2/248 |
| 4,321,710 | A | * | 3/1982 | Off ................................. 2/247 |
| 4,326,302 | A | * | 4/1982 | Lowe et al. ..................... 2/405 |
| 4,683,594 | A | * | 8/1987 | Feinberg ......................... 2/105 |
| 4,838,886 | A | * | 6/1989 | Kent ............................ 604/392 |
| 5,383,867 | A | * | 1/1995 | Klinger ................. 604/385.23 |

(Continued)

FOREIGN PATENT DOCUMENTS

JP    S63-22904-U   A    2/1988

(Continued)

OTHER PUBLICATIONS

International Search Report of PCT/JP2007/068532 issued Nov. 6, 2007.

*Primary Examiner*—Tatyana Zalukaeva
*Assistant Examiner*—Susan Su
(74) *Attorney, Agent, or Firm*—Lowe, Hauptman, Ham & Berner, LLP

(57) ABSTRACT

A disposable diaper enabling the male sex organ to be drawn out easily at the time of urination, which includes: a chassis having at least a front body and a rear body when wearing; a liquid permeable top sheet arranged in at least part of the chassis; a liquid impermeable back sheet on one side in the thickness direction of the top sheet; and a liquid retentive absorber between the top sheet and the back sheet. The chassis has a first chassis and a second chassis. The front body of the chassis has an overlapping section formed by overlapping in at least part of the first and second chassis. The overlapping section has connecting sections for connecting the first and second chassis separated across a substantially center line, which extends in the longitudinal direction of the diaper and divides the width direction into two parts, and a non-connecting section between the connecting sections.

13 Claims, 23 Drawing Sheets

U.S. PATENT DOCUMENTS

| | | | | |
|---|---|---|---|---|
| 5,569,229 | A * | 10/1996 | Rogers | 604/385.09 |
| 5,618,279 | A * | 4/1997 | Pudlo | 604/385.09 |
| 5,716,350 | A * | 2/1998 | Ryan | 604/385.09 |
| 5,810,799 | A * | 9/1998 | Slater | 604/385.09 |
| 5,843,065 | A * | 12/1998 | Wyant | 604/385.09 |
| 5,984,910 | A * | 11/1999 | Berke | 604/352 |
| 6,295,651 | B1 * | 10/2001 | Kang | 2/403 |
| 6,932,800 | B2 * | 8/2005 | LaVon et al. | 604/385.14 |
| 6,986,164 | B1 * | 1/2006 | Morales | 2/94 |
| 6,989,005 | B1 * | 1/2006 | LaVon et al. | 604/385.14 |
| 6,989,006 | B2 * | 1/2006 | Lavon et al. | 604/385.14 |
| 7,175,613 | B2 * | 2/2007 | Sugiyama et al. | 604/385.14 |
| 7,291,137 | B2 * | 11/2007 | LaVon et al. | 604/385.14 |
| 7,381,202 | B2 * | 6/2008 | LaVon et al. | 604/385.14 |
| 7,494,483 | B2 * | 2/2009 | Beck et al. | 604/385.14 |
| 2004/0030311 | A1 * | 2/2004 | Suzuki et al. | 604/367 |
| 2005/0256480 | A1 * | 11/2005 | La Von et al. | 604/385.01 |
| 2006/0241558 | A1 * | 10/2006 | Ramshak | 604/385.09 |
| 2007/0078420 | A1 * | 4/2007 | Sugiyama et al. | 604/361 |
| 2007/0208317 | A1 * | 9/2007 | Krautkramer et al. | 604/385.3 |

FOREIGN PATENT DOCUMENTS

| | | |
|---|---|---|
| JP | 2000-199101 A | 7/2000 |
| JP | 2003-339749 A | 12/2003 |
| JP | 2005-080996 A | 3/2005 |
| JP | 2007-268216 A | 10/2007 |
| JP | 2003-339770 A | 6/2008 |

* cited by examiner

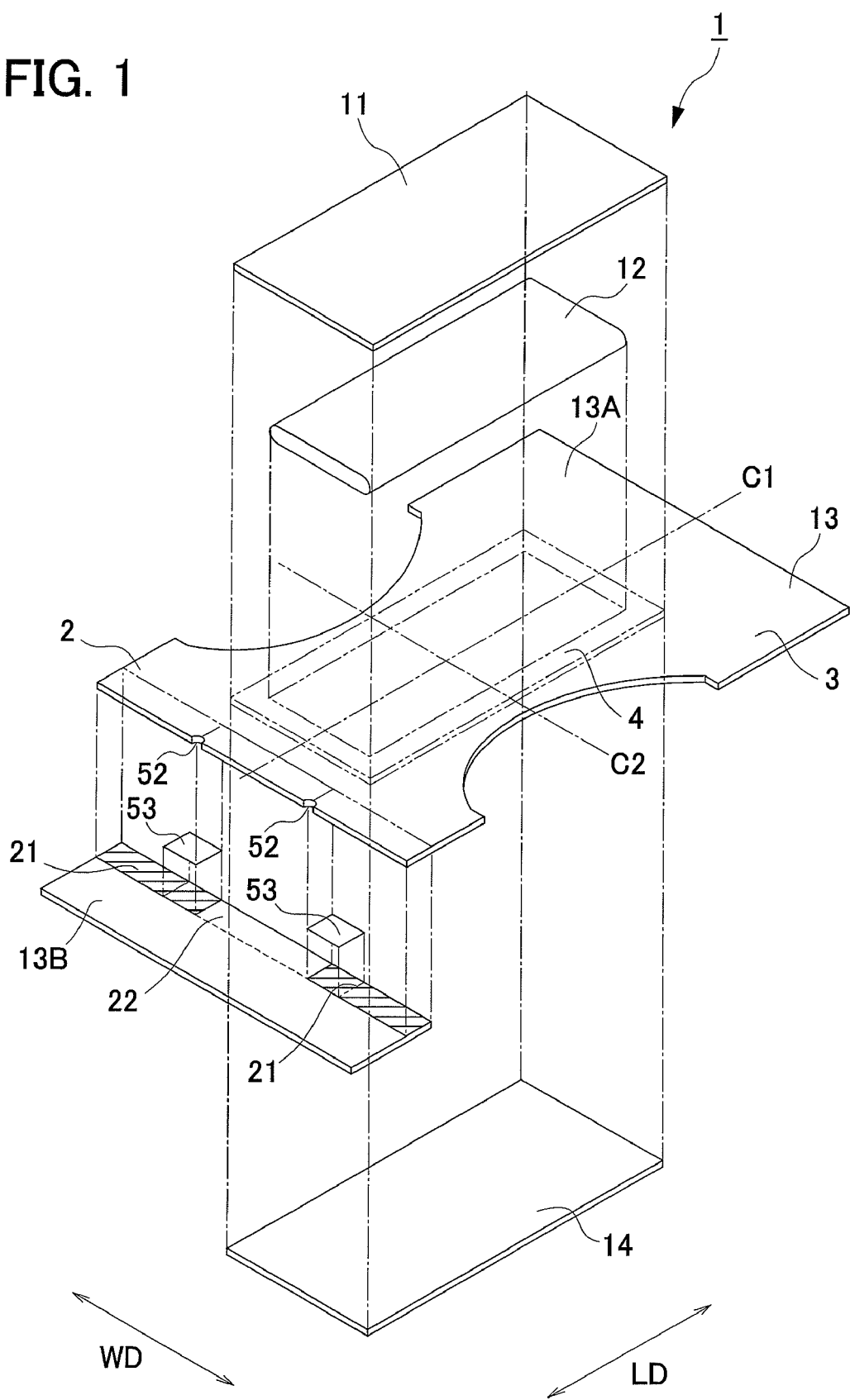

DISPOSABLE DIAPER

This application is based on and claims the benefit of priority from Japanese Patent Applications No. 2006-263365, filed on 27 Sep. 2006, No. 2006-263366, filed on 27 Sep. 2006, and No. 2006-263367, filed on 27 Sep. 2006, the content of which is incorporated herein by reference.

BACKGROUND OF THE INVENTION

1. Field of the Invention

The present invention relates to disposable diapers, and in particular, to disposable diapers enabling the male sex organ to be drawn out easily.

2. Related Art

Conventionally, absorbent articles for use by elderly persons, physically disabled, etc., including, for example, disposable diapers, training underpants, and incontinent underpants have been proposed. The absorbent articles are properly used in accordance with a wearer's lifestyle and care level. For example, disposable diapers are intended for elderly persons and physically disabled who have difficulty in excretory function, and are used as auxiliary tools for excretion, or alternatively as sanitary goods for care, by retaining and absorbing excrement without leakage.

In some cases, disposable diapers may be used not only by persons who have difficulties in urination on their own, but also by persons who can urinate on their own, such as physically disabled of mild incontinence and elderly persons who can walk. However, the physically disabled of mild incontinence and the elderly persons who can walk are often reluctant to wear a diaper, due to the impression that diapers are usually intended to be used by persons who have difficulties in urinating on their own. This is because, for leak prevention purposes, the conventional diapers do not have such an urination opening, etc. for drawing out the male sex organ, as typical male underwear. Hence, when a wearer urinates, the wearer has to enter a single room, etc., and perform a different action from a usual urinating action at the time of urination, such as removal of the diaper. This action is very complicated, especially for male wearers, thereby increasing the reluctance to wear the diaper.

Japanese Unexamined Patent Application Publication No. 2005-080996 discloses an absorbent article that enables drawing out of the male sex organ, even when a diaper is worn.

The absorbent article disclosed in the above Publication includes an inner sheet, an outer sheet, and an intermediate sheet disposed therebetween. The absorbent article further includes a paper-diaper main body that can be divided into an abdomen part positioned on the abdomen of a wearer wearing the absorbent article, a back part positioned on the back thereof, and a crotch part disposed therebetween, and an absorber stuck to the crotch part of the paper-diaper main body. The inner and outer sheets of the abdomen part are formed with perforations for forming openings through which the male sex organ can be drawn out when worn. By disengaging a fastening member and shifting the intermediate sheet, the openings of the inner and outer sheets communicate with each other so as to form a through hole in the abdomen part. This enables the wearer to draw out the male sex organ, even when wearing the paper diaper.

However, with the paper diaper disclosed in the above Publication, it is difficult to widen the opening for drawing out the male sex organ, which is formed in the inner and outer sheets of the abdomen part as simple openings. When the wearer urinates, the paper diaper requires various actions for drawing out the male sex organ from the opening. For example, when drawing out the male sex organ, he has to disengage the fastening member of the intermediate sheet to shift the intermediate sheet. This makes it difficult for the wearer, who may only be able to use one hand due to paralysis, etc., to urinate on his own. Moreover, a peculiar sound is liable to be generated when the intermediate sheet is separated from the fastening member. Therefore, when the wearer urinates, others might be aware that he is wearing the paper diaper. This increases the reluctance to use the paper diaper.

SUMMARY OF THE INVENTION

The present invention has been made in view of the foregoing problem, and aims at providing a disposable diaper that enables easy drawing out of the male sex organ at the time of urination.

In order to achieve the above aim, the present inventor has completed the invention based on the finding that urination is facilitated by the arrangement in which an opening for urination formed by stacking a plurality of sheet members one upon another is disposed in a front body of a disposable diaper, and a predetermined location of the disposable diaper is so formed as to be expandable and contractible. Specifically, the present invention provides the following disposable diapers.

The disposable diaper of a first aspect of the present invention includes: a chassis having at least a front body and a rear body when wearing; a liquid permeable top sheet arranged at least in part of the chassis; a liquid impermeable back sheet arranged on one side in a thickness direction of the top sheet; and a liquid retentive absorber disposed between the top sheet and the back sheet. The chassis has a first chassis and a second chassis. The front body of the chassis includes an overlapping section to be formed by overlapping in at least part of the first and second chassis with each other. The overlapping section has connecting sections and a non-connecting section provided between the connecting sections. The connecting sections connect the first and second chassis disposed in regions separated from each other across a substantially center line extending in a longitudinal direction of the disposable diaper and dividing a width direction into two parts.

In a second aspect of the disposable diaper as described in the first aspect of the present invention, reinforcing members having high rigidity are provided in at least part of the connecting sections, respectively.

According to a third aspect of the present invention, a disposable diaper includes: a chassis having at least a front body and a rear body when worn; a liquid permeable top sheet arranged in at least part of the chassis; a liquid impermeable back sheet arranged on one side in a thickness direction of the top sheet; and a liquid retentive absorbent body provided between the top sheet and the back sheet. The front body of the chassis has an openable section and an auxiliary sheet provided so as to cover the openable section. The openable section is formed so that it can separate a predetermined location of the chassis in the front body, along a cutting guide line extending in a longitudinal direction of the disposable diaper and connecting points separated from each other across a substantially center line dividing a width direction into two parts.

According to a fourth aspect of the present invention, in the disposable diaper as described in the third aspect, hole portions are provided at two ends of the openable section, respectively.

According to a fifth aspect of the present invention, in the disposable diaper as described in the third of fourth aspect, reinforcing members having high rigidity are provided at the two ends of the openable section, respectively.

According to a sixth aspect of the present invention, a disposable diaper includes: a chassis having at least a front body and a rear body when worn; a liquid permeable top sheet arranged in at least part of the chassis; a liquid impermeable back sheet arranged on one side in a thickness direction of the top sheet; and a liquid retentive absorber provided between the top sheet and the back sheet. The front body of the chassis has an opening and an auxiliary sheet provided so as to cover the opening. The opening is composed of at least one of a line and a pattern extending in a longitudinal direction of the disposable diaper and connecting points separated from each other across a substantially center line dividing a width direction into two parts.

According to a seventh aspect of the present invention, in the disposable diaper as described in the sixth aspect, predetermined shaped hole portions are provided at two ends of the opening, respectively.

According to an eighth aspect of the present invention, in the disposable diaper as described in the sixth or seventh aspect, reinforcing members having high rigidity are provided at the two ends of the opening, respectively.

Thus, the present invention can provide the disposable diapers permitting easy drawing out of the male sex organ at the time of urination.

BRIEF DESCRIPTION OF THE DRAWINGS

FIG. 1 is a perspective exploded assembly drawing in the flattened state of a disposable diaper according to a first embodiment of the present invention;

FIG. 3A is a perspective view showing a state in which a pants-type (or underpants-type) disposable diaper is put on;

FIG. 3B is a perspective view showing a state in which an expansion-type disposable diaper is put on;

FIG. 10 is a perspective view showing a state in which the disposable diaper in the first embodiment is put on;

FIG. 12 is a perspective view showing a state in which the disposable diaper according to another example of the first embodiment is put on;

DETAILED DESCRIPTION OF THE INVENTION

Embodiments of the present invention are described below with reference to the accompanying drawings. However, it is to be understood that the embodiments of the present invention are not limited to the following, and the technical scope of the present invention is not limited to these. Although the following embodiment describes an adult disposable diaper by way of example and without limitation, the present invention may be applied to a child disposable diaper for toilet training.

In the following preferred embodiments, it is assumed that the side of the disposable diaper facing a wearer's body is a skin-contacting side, and the side opposite the skin-contacting side is a skin-noncontacting side.

Figure 2A:
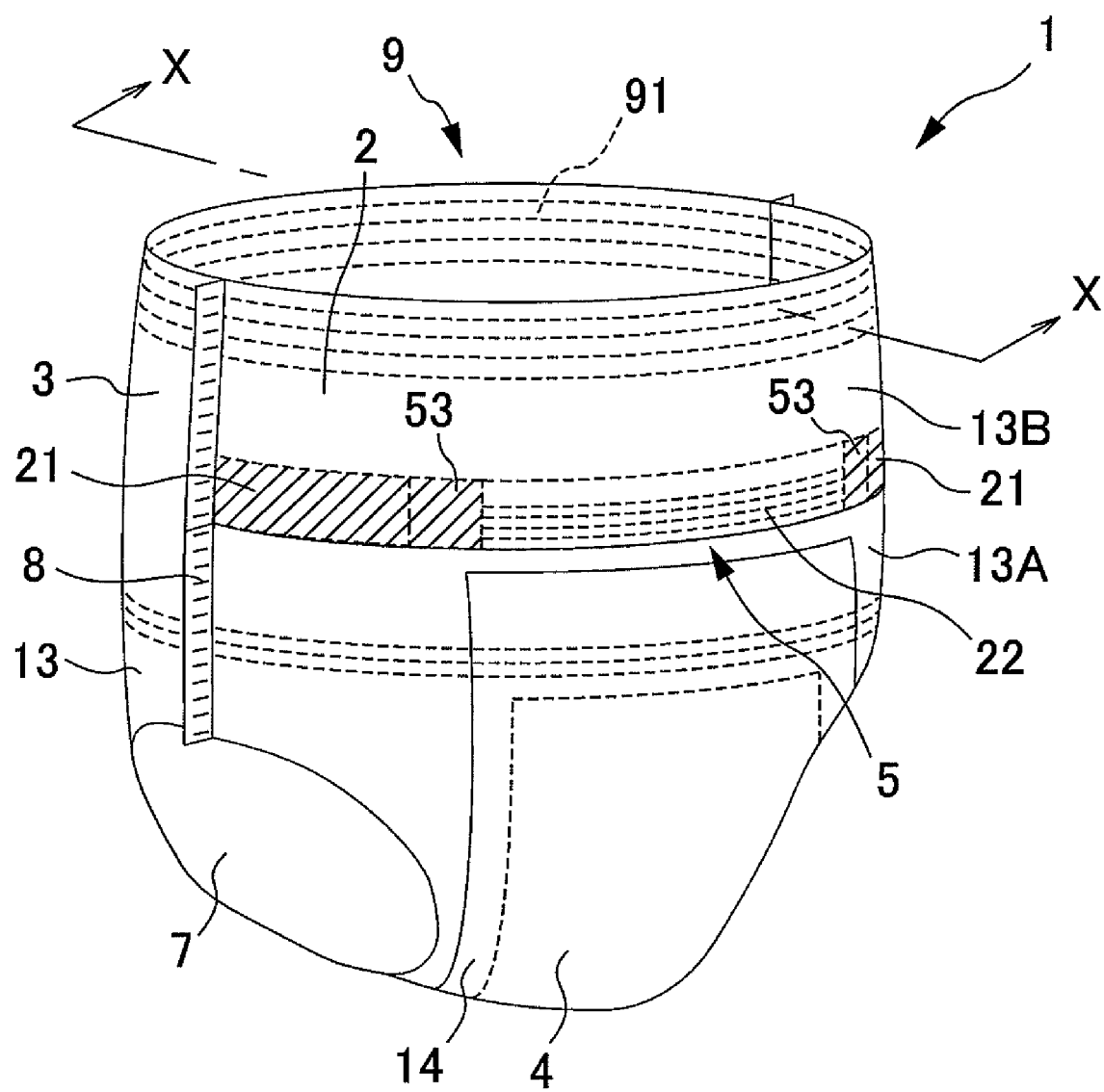
FIG. 2A is a perspective view of the disposable diaper of the first embodiment.
Figure 2B:
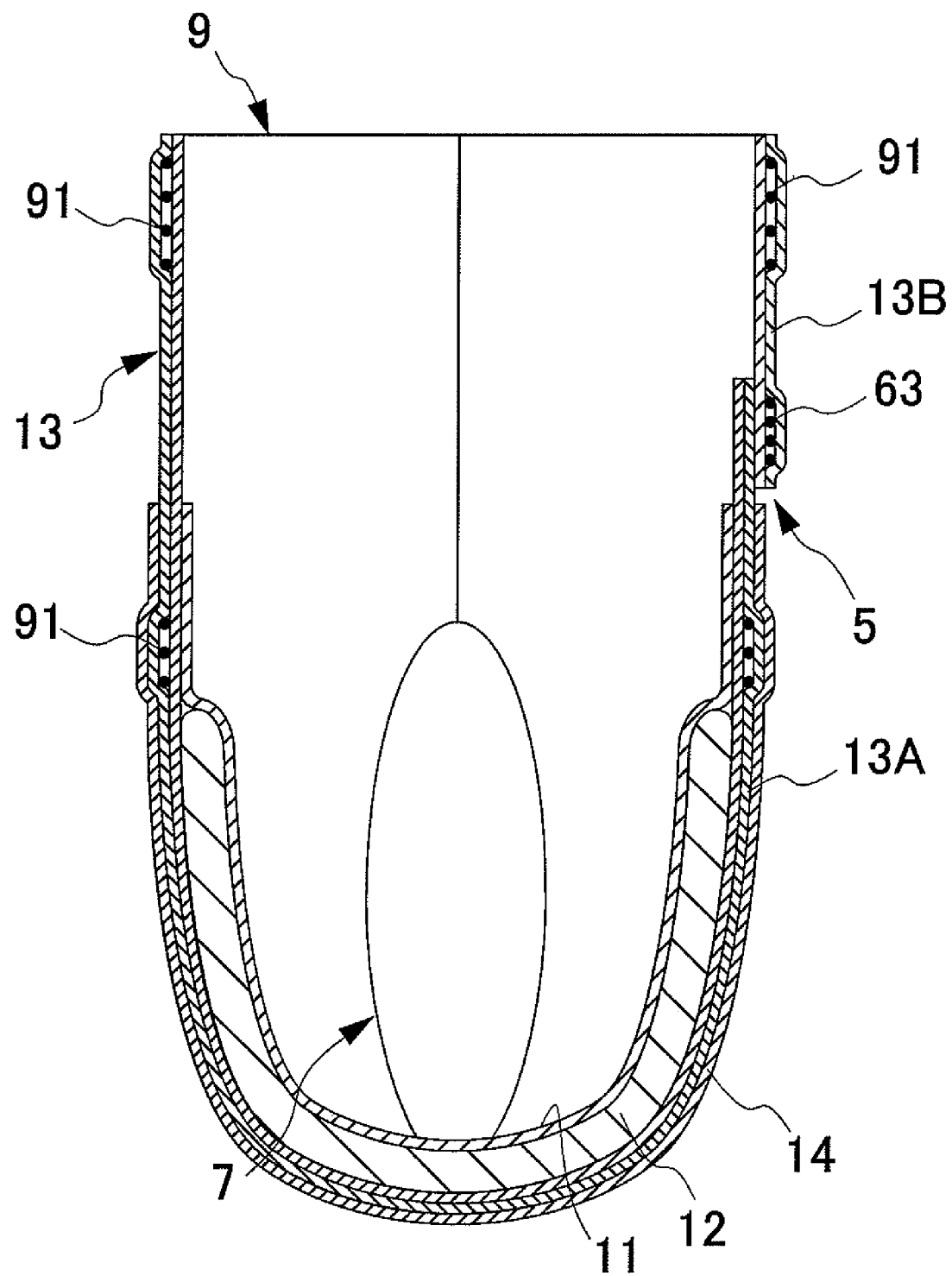
FIG. 2B is a cross-sectional view taken along the line X-X in FIG. 2A.
Figure 3A:
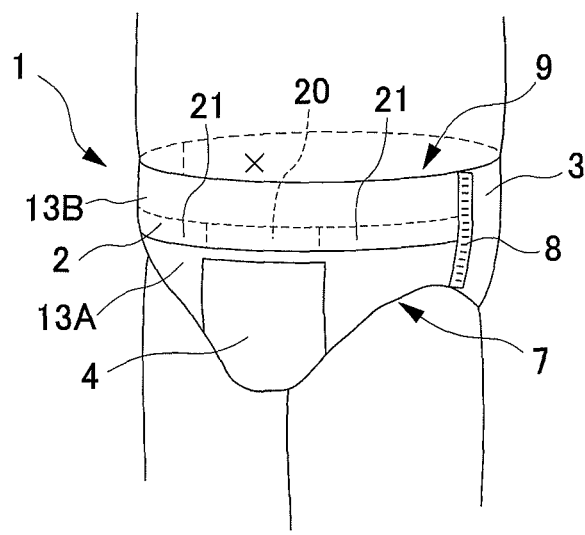
Figure 3B:
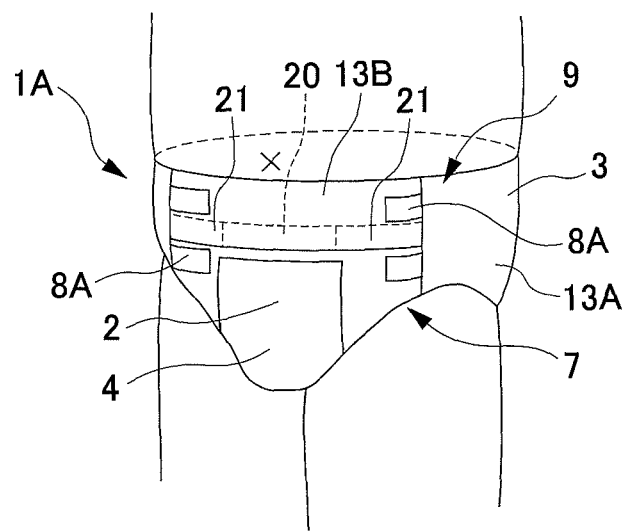
Figure 4A:
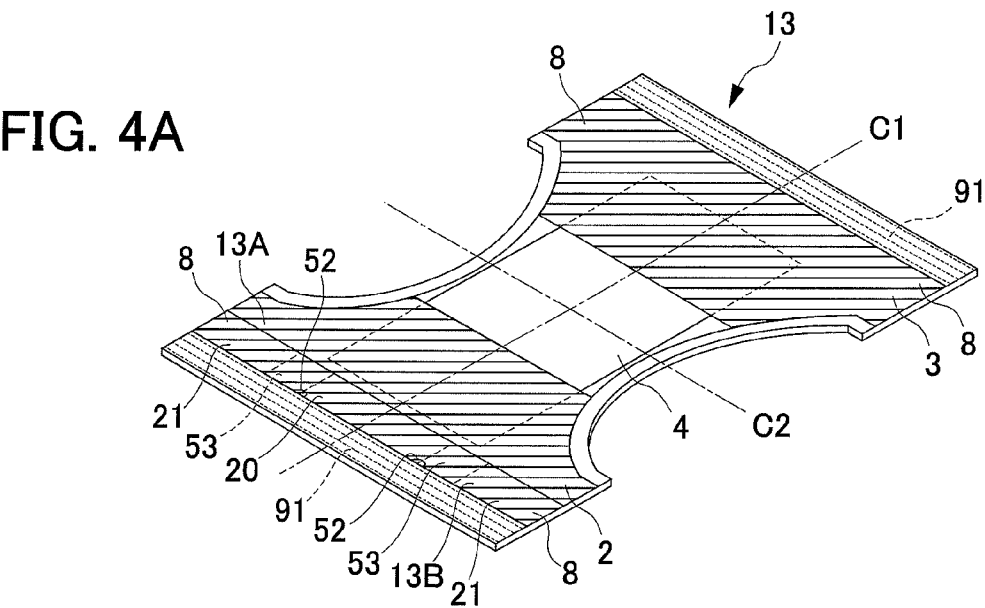
FIG. 4A is a flattened diagram showing a layout of an elastic sheet of the pants-type disposable diaper in the first embodiment.
Figure 4B:
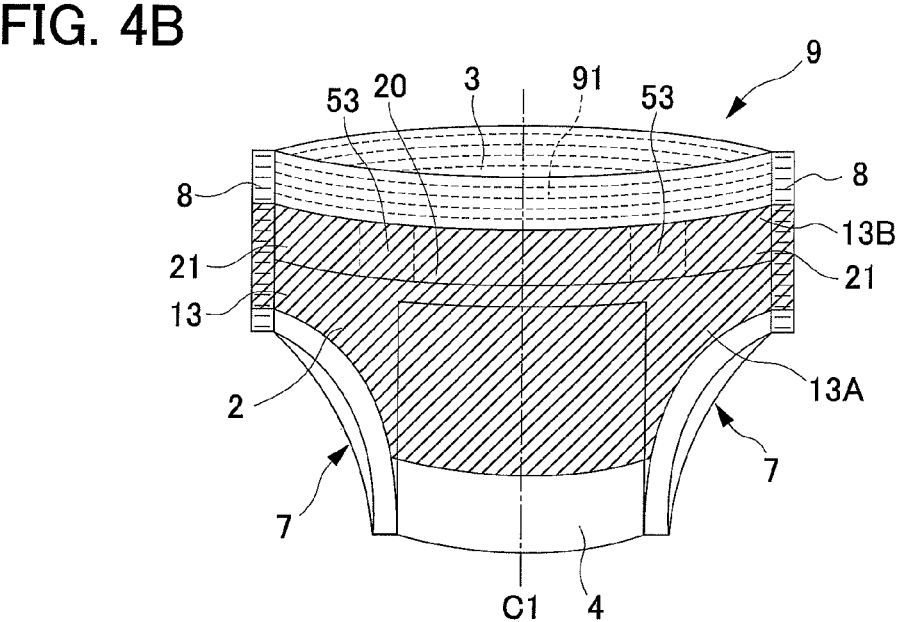
FIG. 4B is a front view showing the layout of the elastic sheet of the pants-type disposable diaper in the first embodiment.
Figure 5:
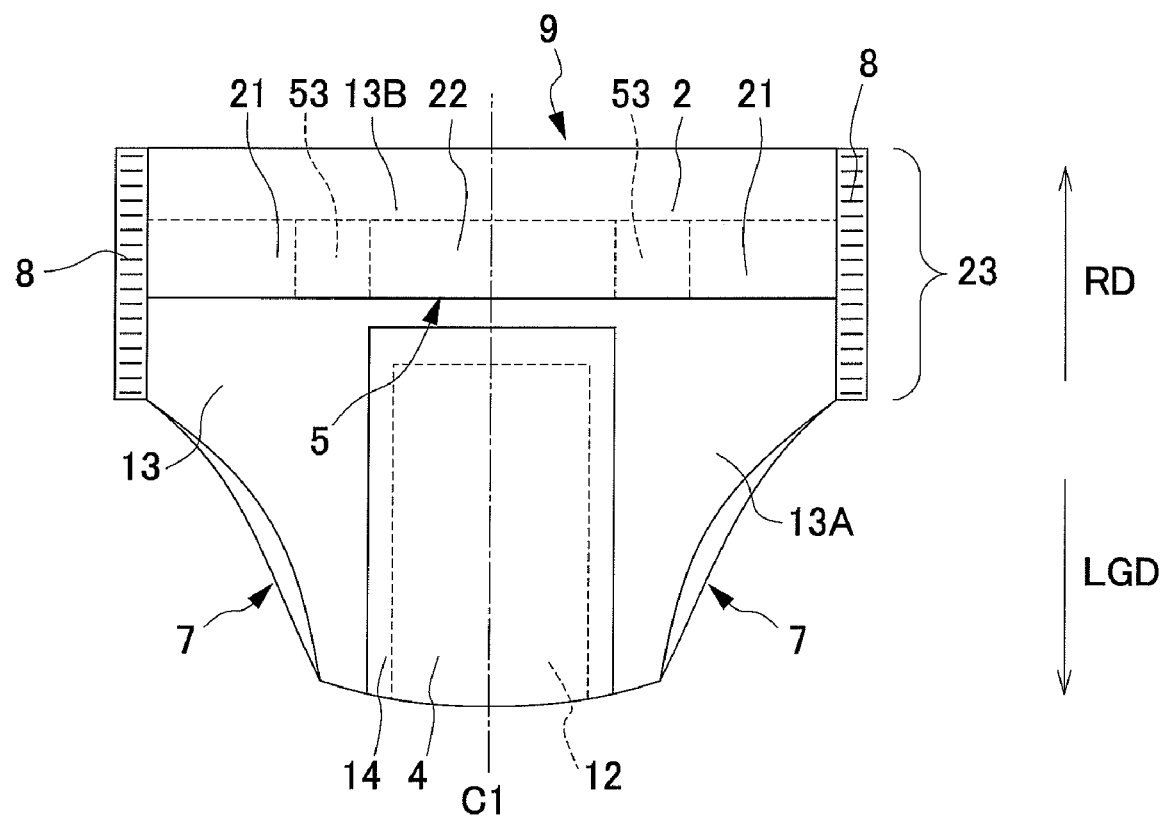
FIG. 5 is a front view showing a position of an overlapping opening of the pants-type disposable diaper in the first embodiment.
Figure 6A:
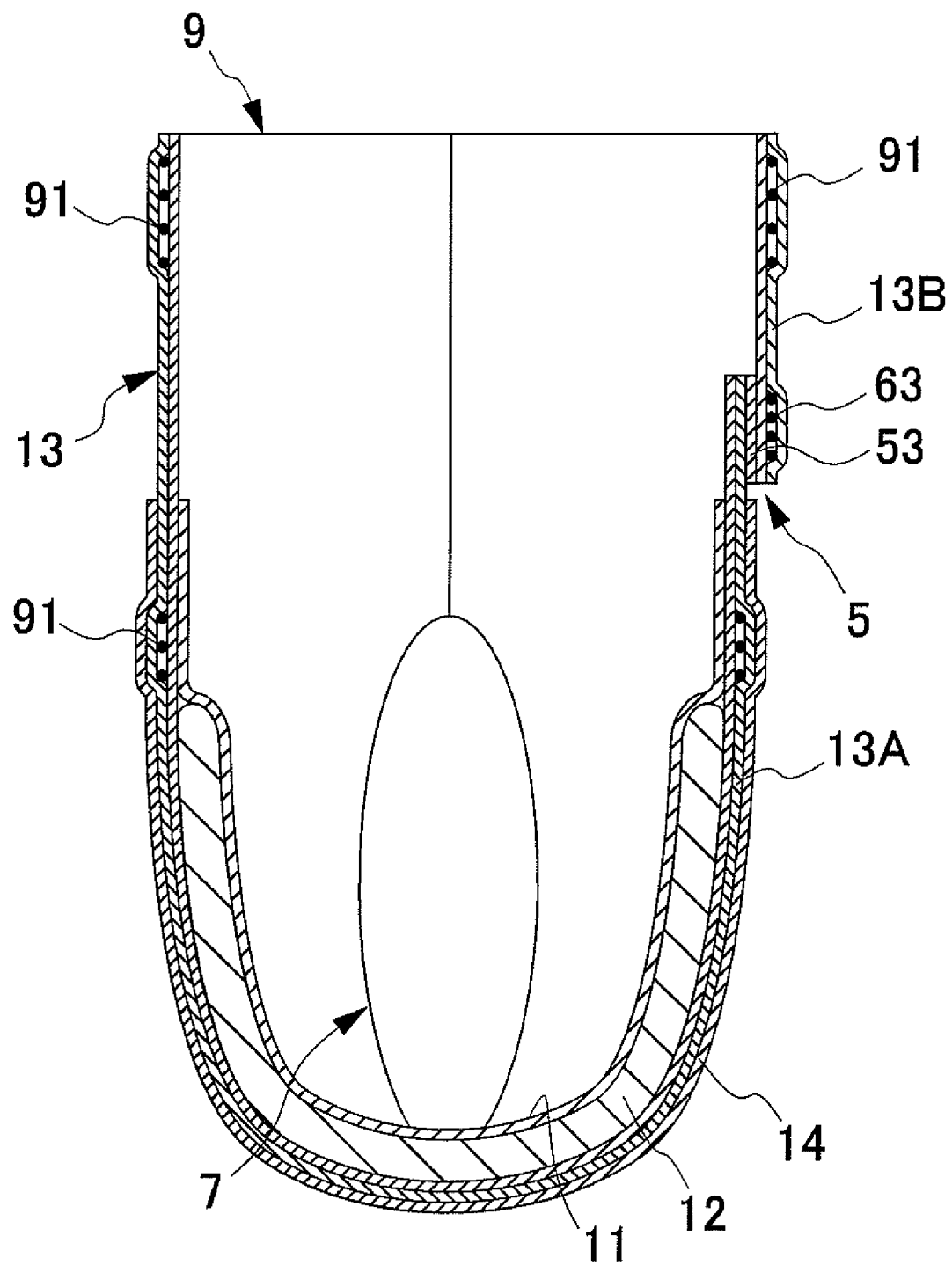
FIG. 6A is a sectional view showing a state in which a first chassis and a second chassis are connected to each other.
Figure 6B:
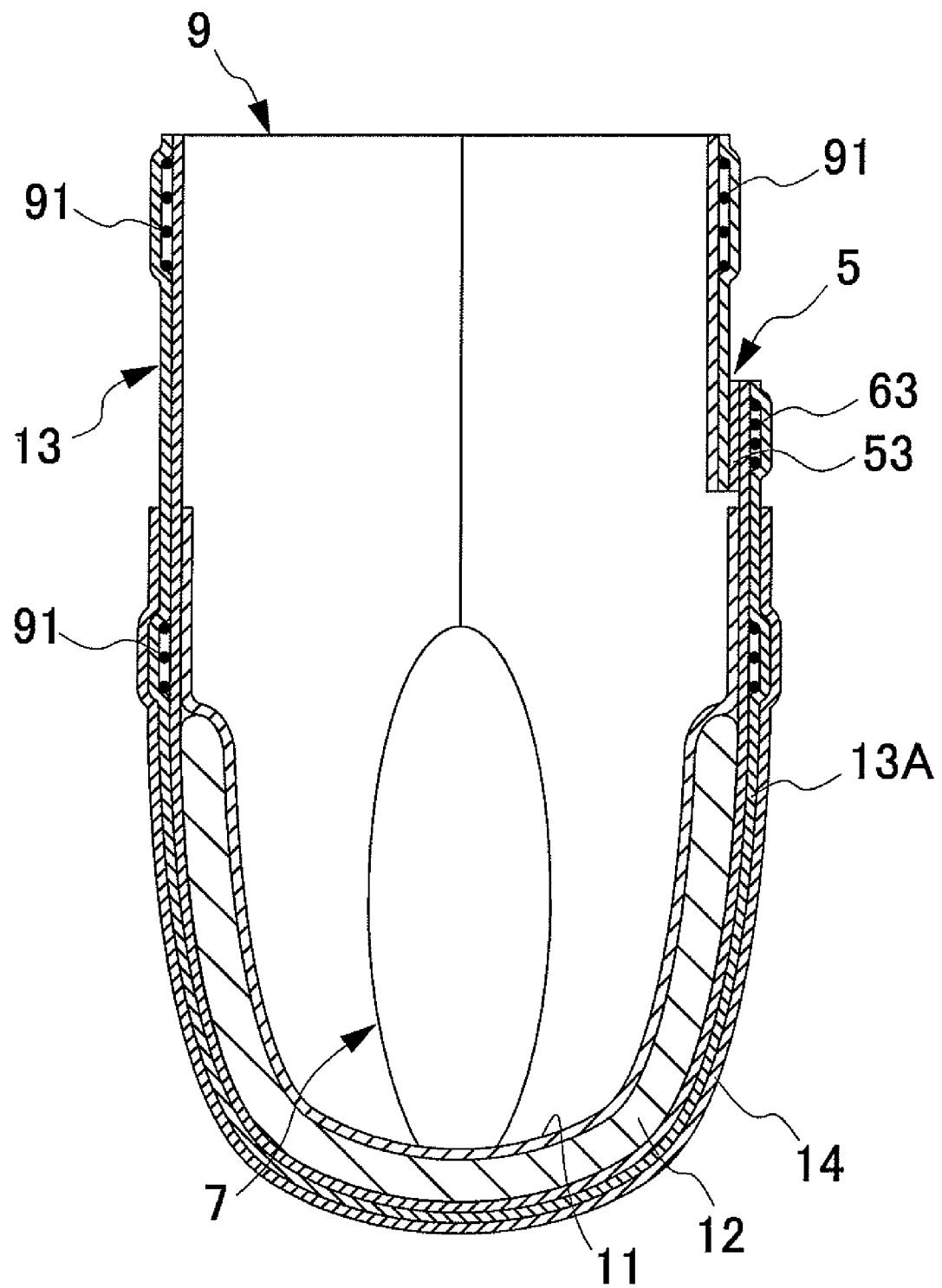
FIG. 6B is a sectional view showing another state in which the first and second chassis are connected to each other.
Figure 7A:
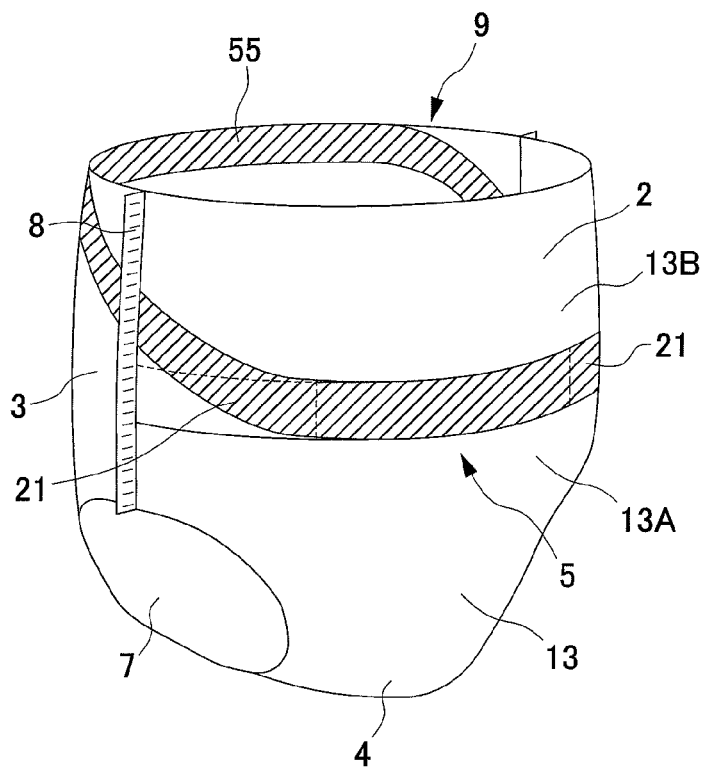
FIG. 7A is a perspective view showing an opening stretchable region of the disposable diaper in the first embodiment.
Figure 7B:
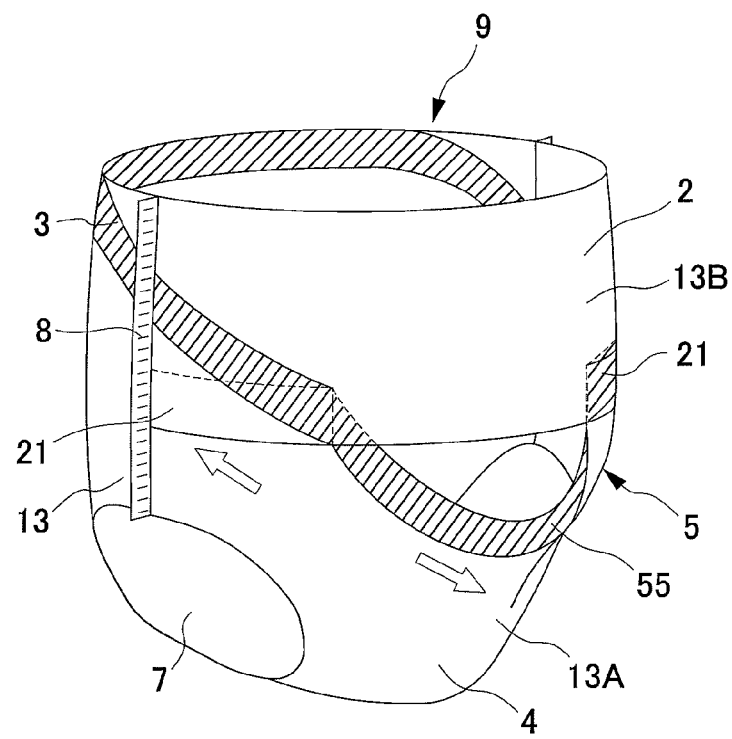
FIG. 7B is a perspective view showing a state in which the overlapping opening is opened by expansion and contraction of the opening stretchable region.
Figure 8A:
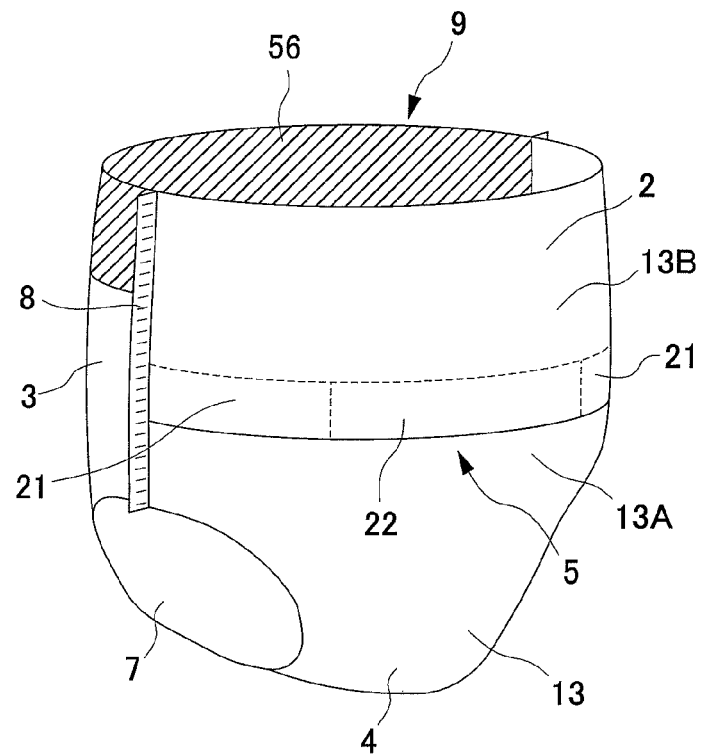
FIG. 8A is a perspective view showing an elastic back body region of the disposable diaper in the first embodiment.
Figure 8B:
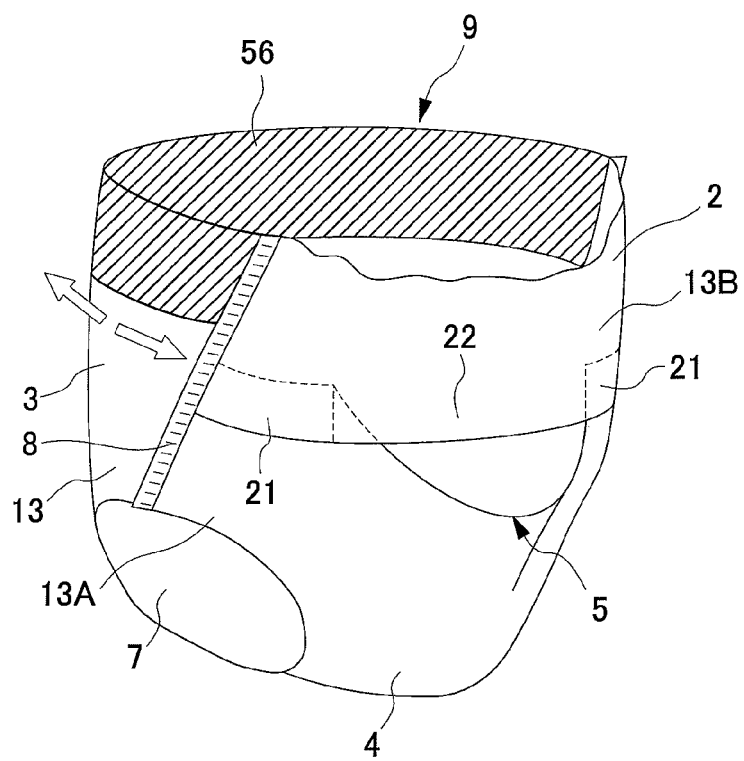
FIG. 8B is a perspective view showing a state in which the overlapping opening is opened by expansion and contraction of the elastic back body region.
Figure 9A:
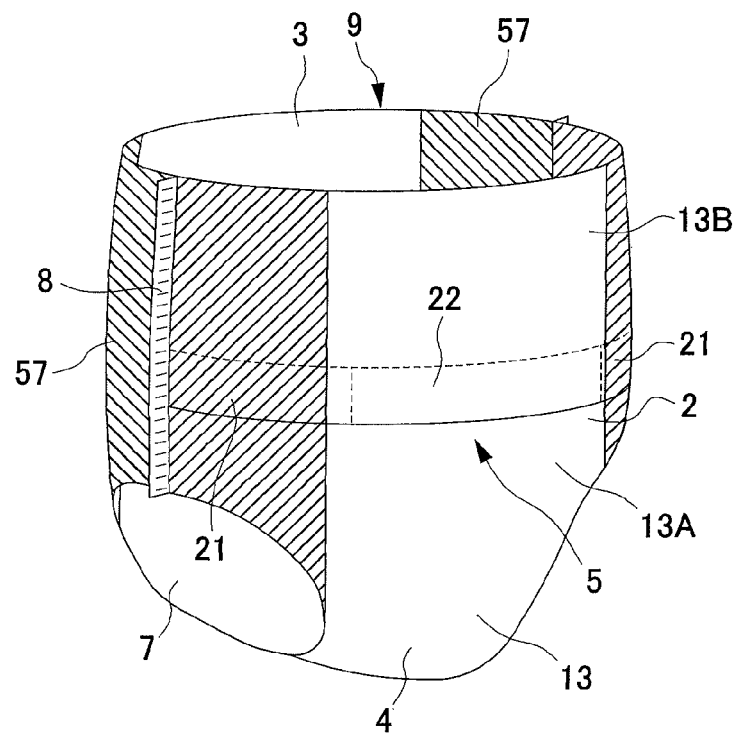
FIG. 9A is a perspective view showing an elastic boundary region of the disposable diaper in the first embodiment.
Figure 9B:
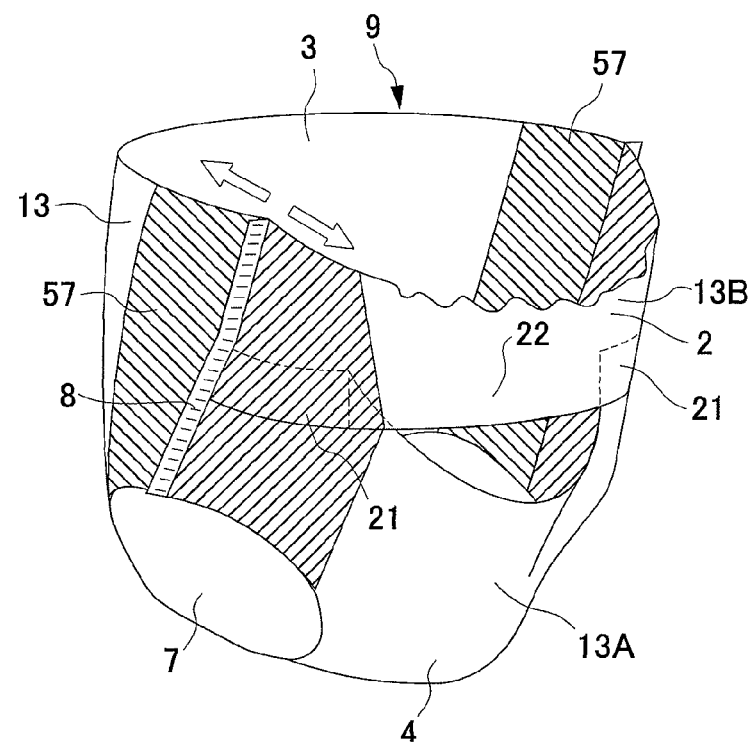
FIG. 9B is a perspective view showing a state in which the overlapping opening is opened by expansion and contraction of the elastic boundary region.
Figure 10:
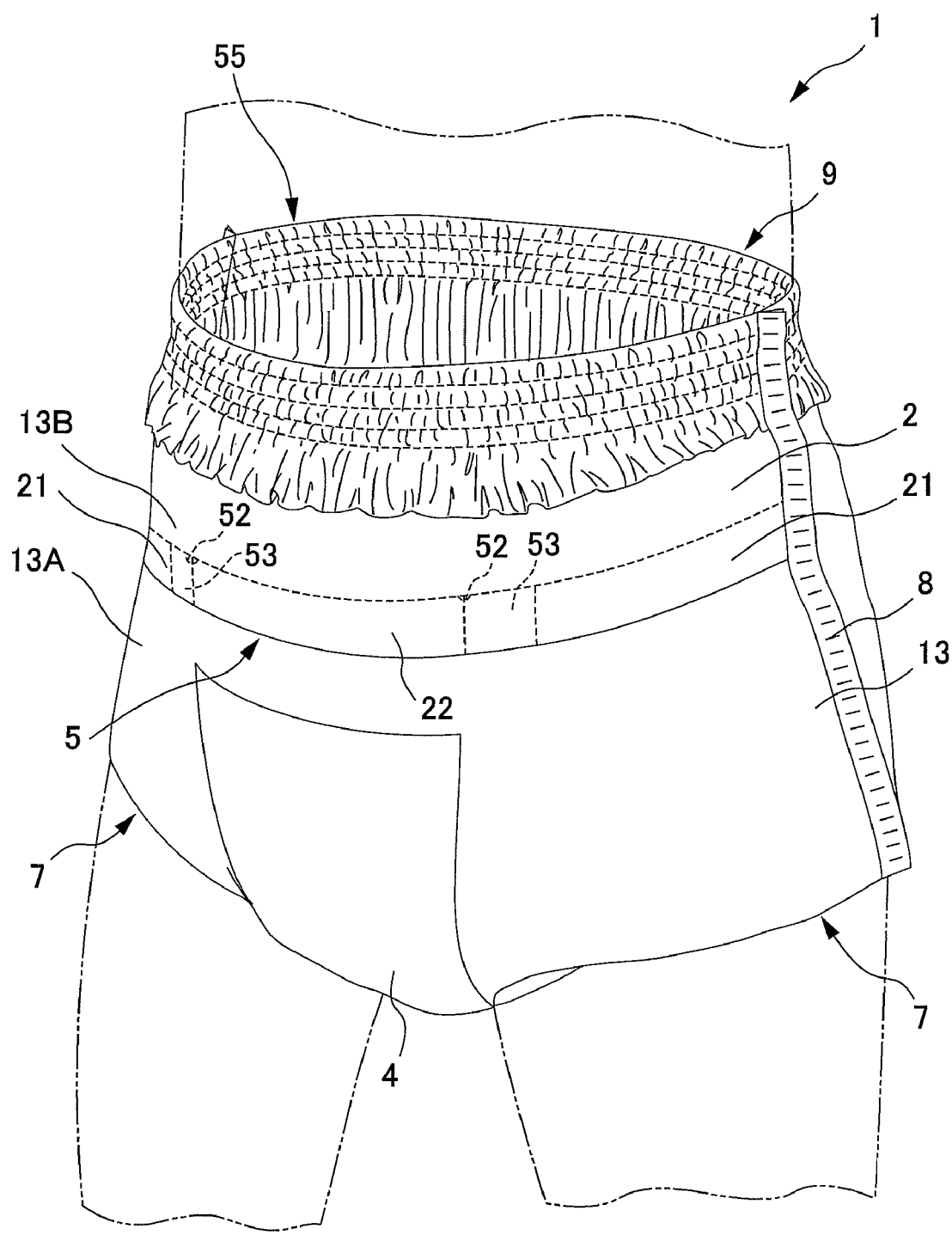

FIG. 1 is a perspective exploded assembly drawing in the flattened state of a disposable diaper according to a first embodiment of the present invention. FIG. 2A is a perspective view of the disposable diaper of the first embodiment. FIG. 2B is a cross-sectional view taken along the line X-X in FIG. 2A. FIG. 3A is a perspective view showing a state in which a pants-type disposable diaper is put on. FIG. 3B is a perspective view showing a state in which an expansion-type disposable diaper is put on. FIG. 4A is a flattened diagram showing a layout of an elastic sheet of the pants-type disposable diaper in the first embodiment. FIG. 4B is a front view showing the layout of the elastic sheet of the pants-type disposable diaper according to the first embodiment. FIG. 5 is a front view showing a position of an overlapping opening of the pants-type disposable diaper in the first embodiment. FIG. 6A is a sectional view showing a state in which first and second chassis are connected to each other. FIG. 6B is a sectional view showing another state in which the first and second chassis are connected to each other. FIG. 7A is a perspective view showing an opening stretchable region of the disposable diaper in the first embodiment. FIG. 7B is a perspective view showing a state in which the overlapping opening is opened by expansion and contraction of the opening stretchable region. FIG. 8A is a perspective view showing an elastic back body region of the disposable diaper in the first embodiment. FIG. 8B is a perspective view showing a state in which the overlapping opening is opened by expansion and contraction of the elastic back body region. FIG. 9A is a perspective view showing an elastic boundary region of the disposable diaper in the first embodiment. FIG. 9B is a perspective view showing a state in which the overlapping opening is opened by expansion and contraction of the elastic boundary region. FIG. 10 is a perspective view showing a state in which the disposable diaper in the first embodiment is put on.

Figure 11:
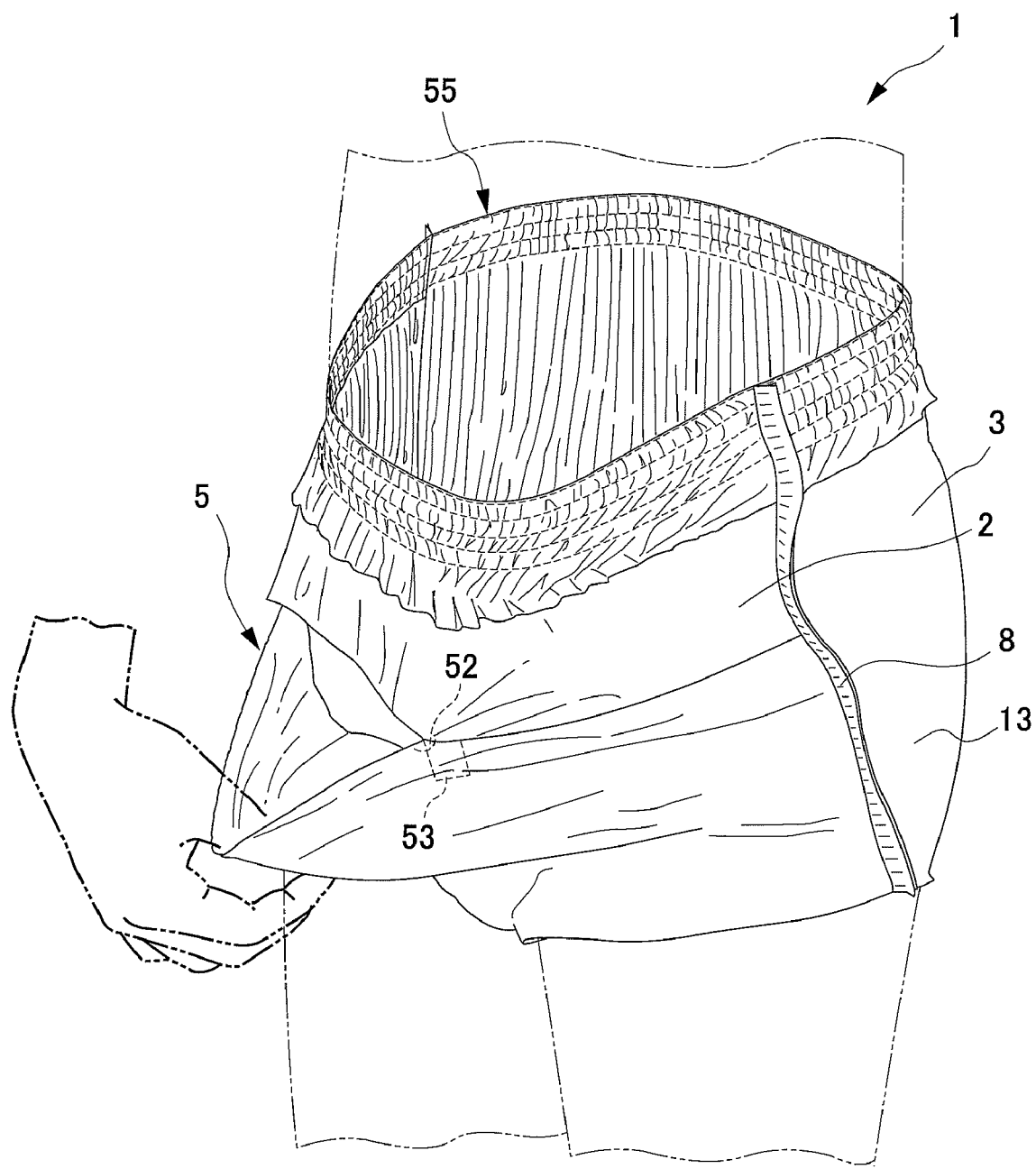
FIG. 11 is a perspective view showing a state in which the overlapping opening is opened.
Figure 12:
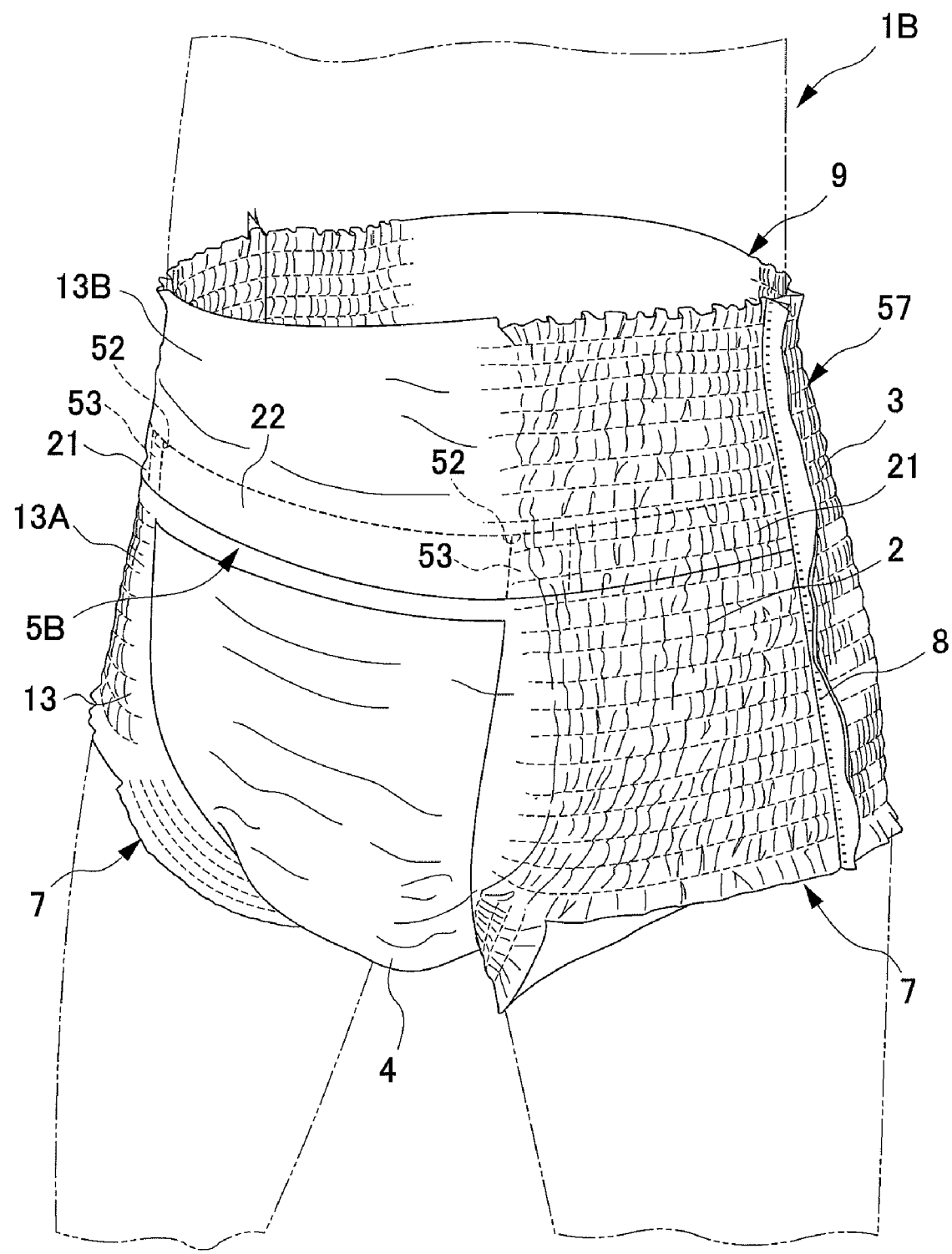
Figure 13:
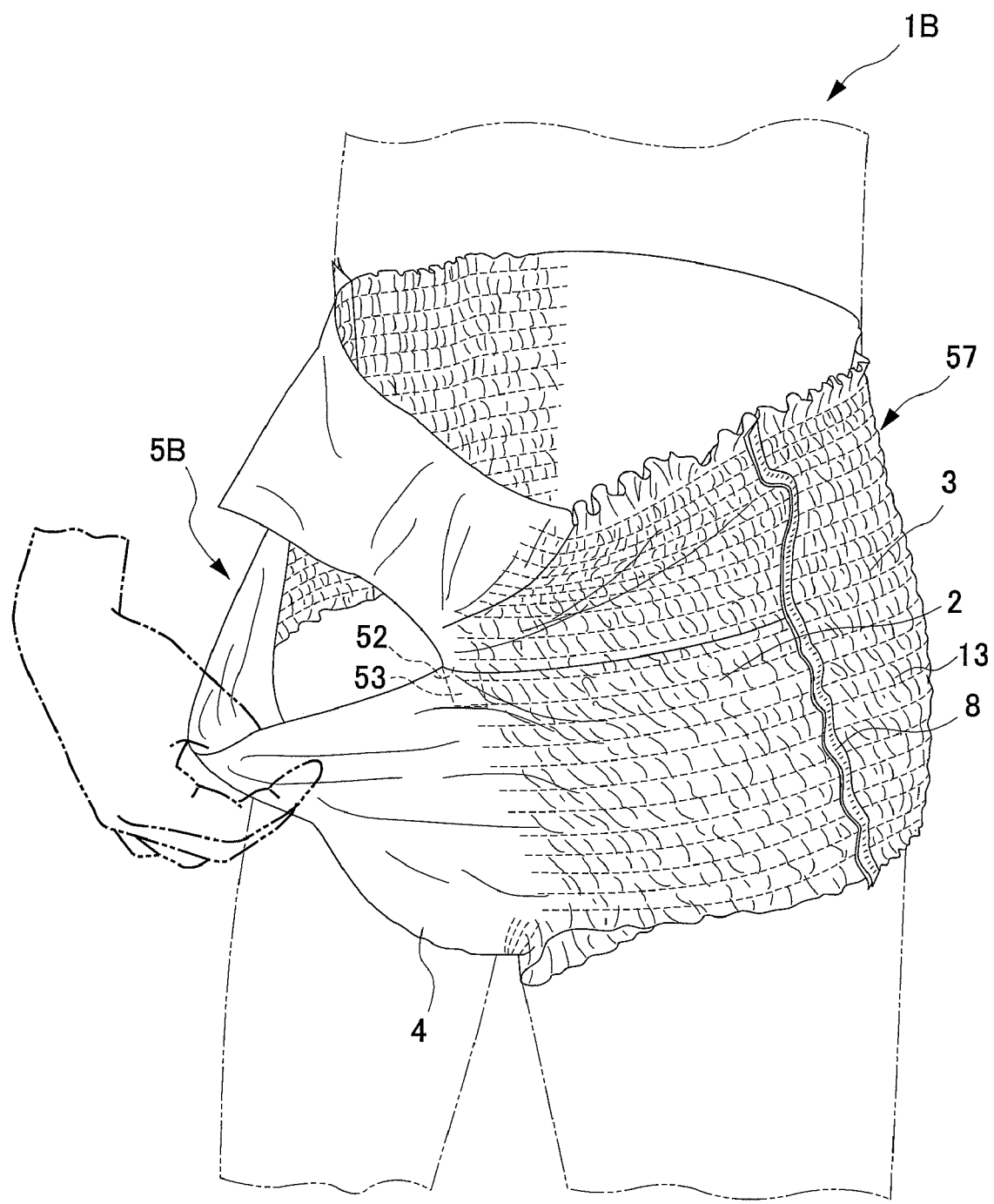
FIG. 13 is a perspective view showing a state in which the overlapping opening of FIG. 12 is opened.
Figure 14:
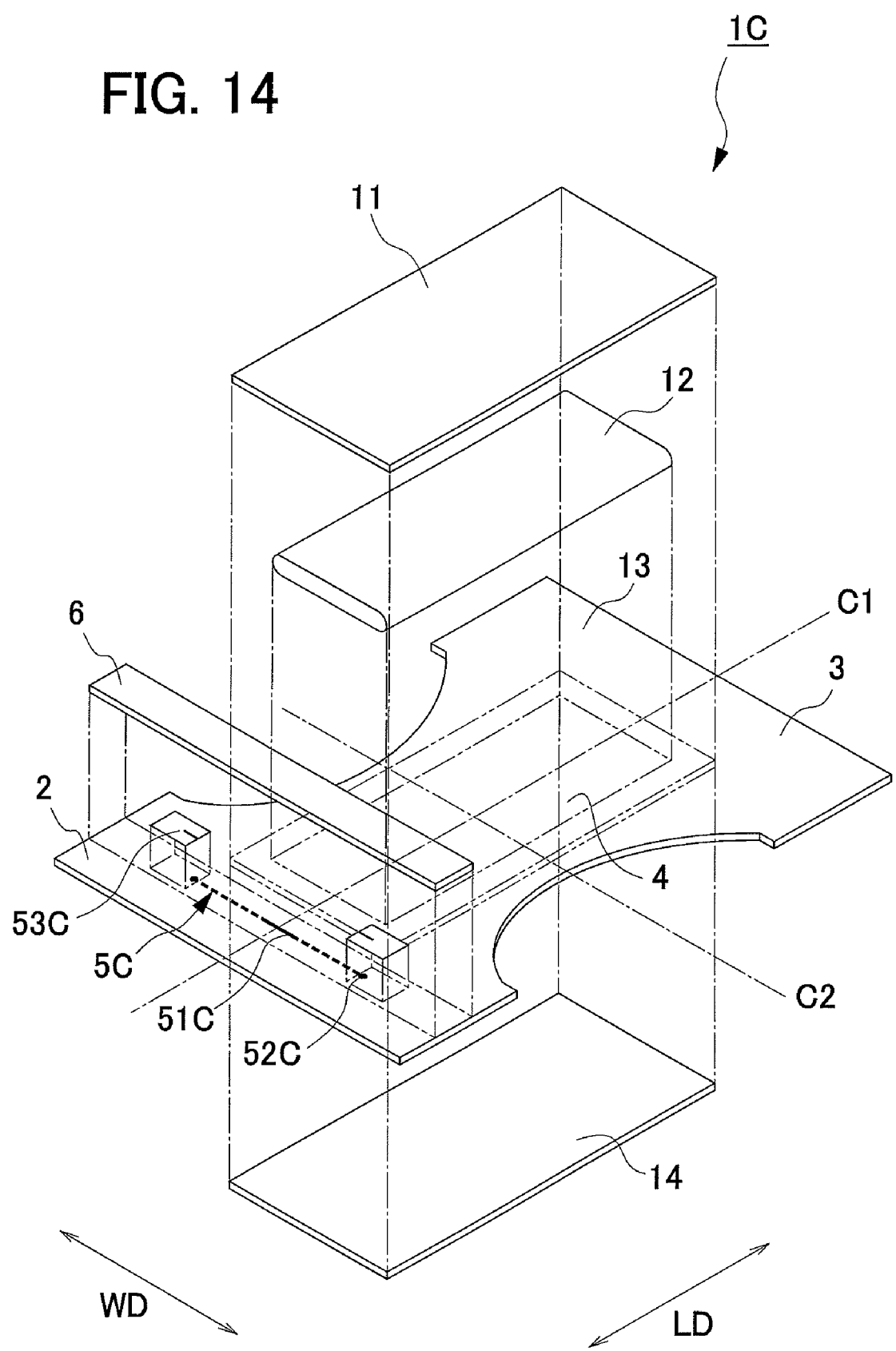
FIG. 14 is a perspective exploded assembly drawing in the developed state of a disposable diaper according to a second embodiment of the present invention.
Figure 15A:
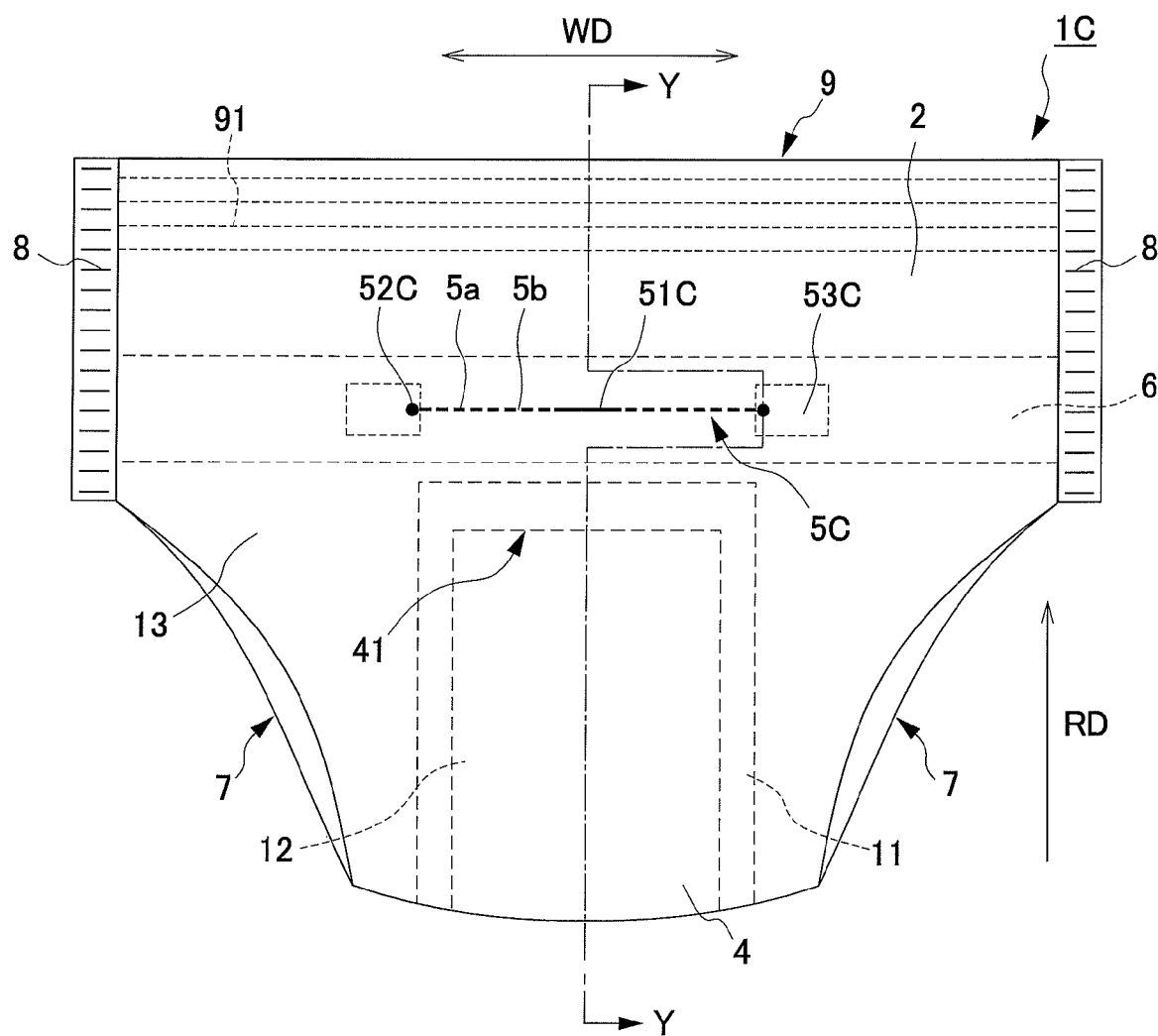
FIG. 15A is a front view of the disposable diaper of the second embodiment.
Figure 15B:
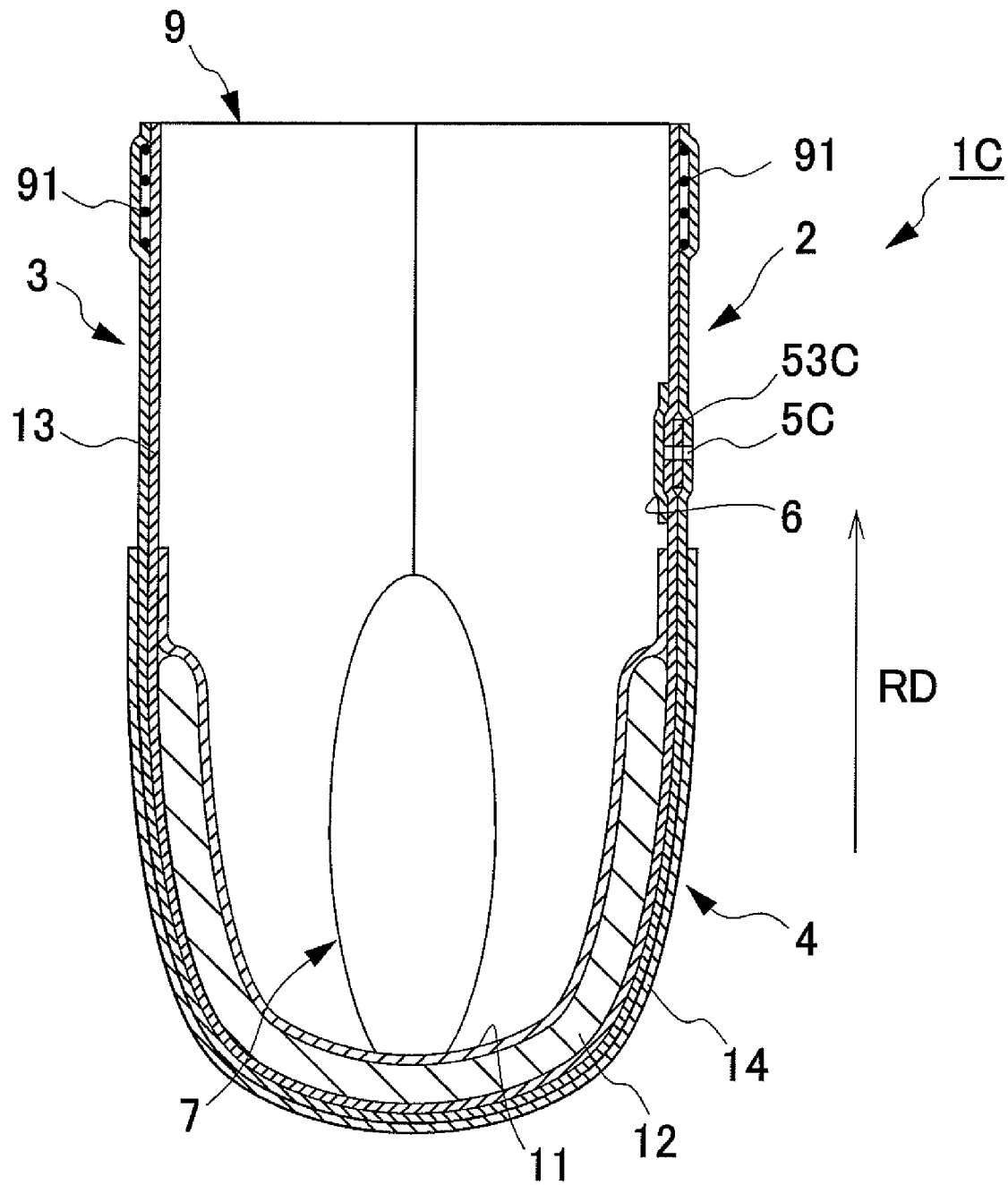
FIG. 15B is a cross-sectional view taken along the line Y-Y in FIG. 15A.
Figure 16A:
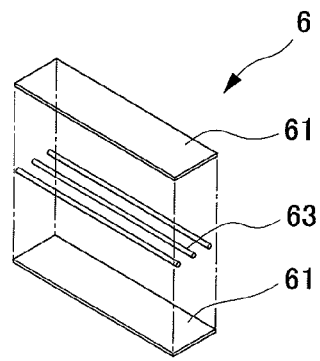
FIG. 16A is a perspective view showing a masking sheet as an auxiliary sheet.
Figure 16B:
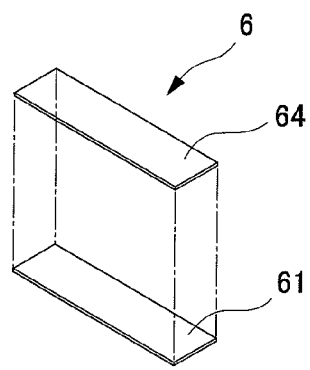
FIGS. 16B and 16C are perspective views showing other examples of the masking sheet, respectively.
Figure 16C:
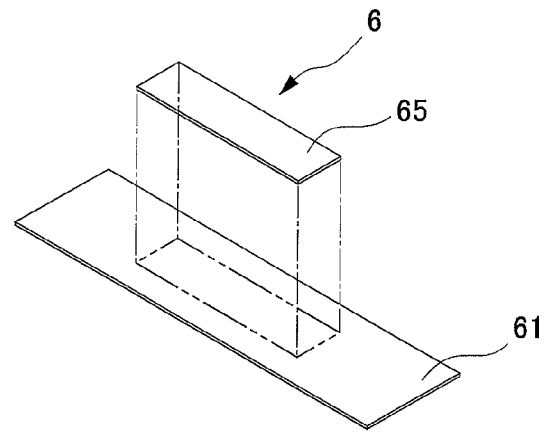
Figure 17A:
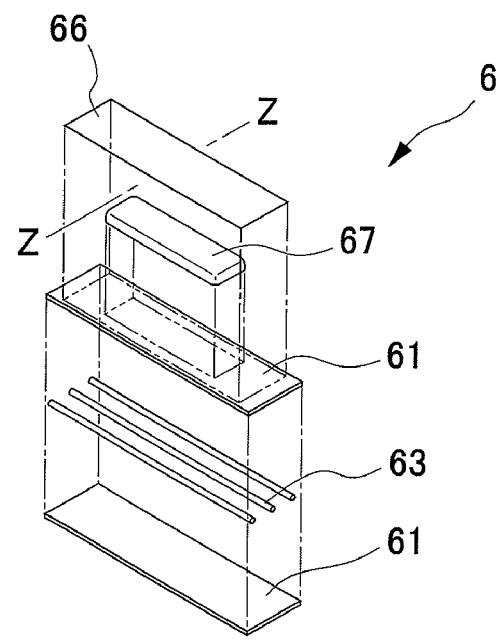
FIG. 17A is an exploded perspective view of a masking sheet where an absorptive member is arranged.
Figure 17B:
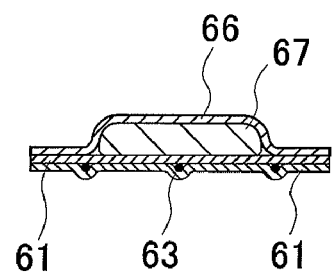
FIG. 17B is a cross-sectional view taken along the line Z-Z of FIG. 17A.
Figure 18A:
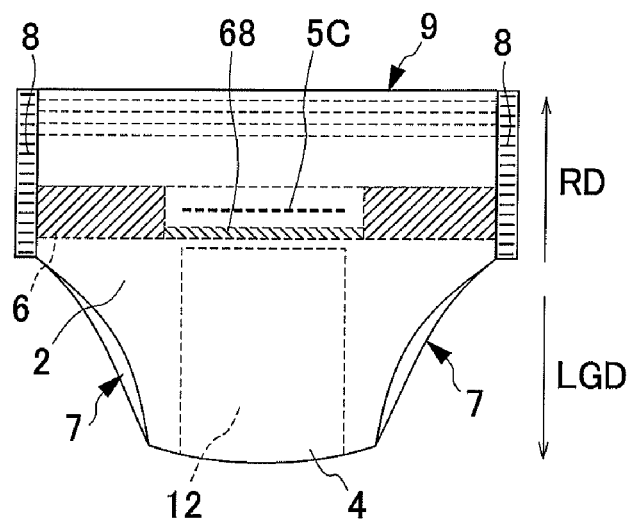
FIG. 18A is a front view showing a connection state of the masking sheet.
Figure 18B:
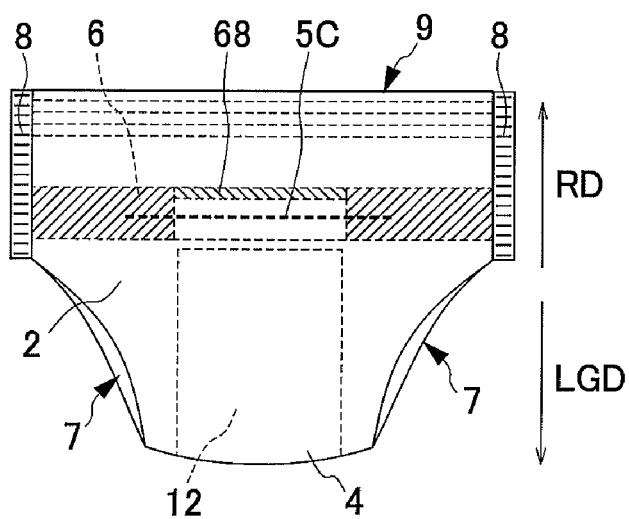
FIG. 18B is a front view showing another connection state of the masking sheet.
Figure 19A:
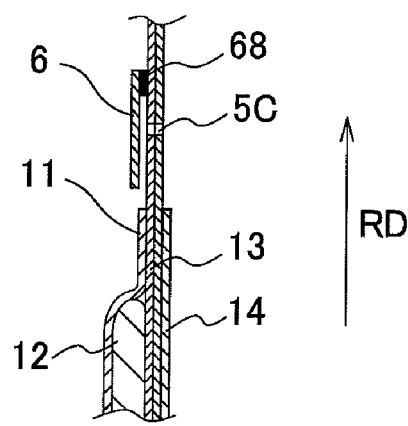
FIG. 19A is a cross-sectional view showing a connection state of the masking sheet.
Figure 19B:
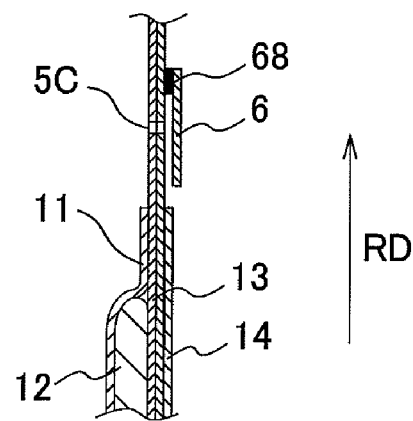
FIG. 19B is a cross-sectional view showing another connection state of the masking sheet.
Figure 20:
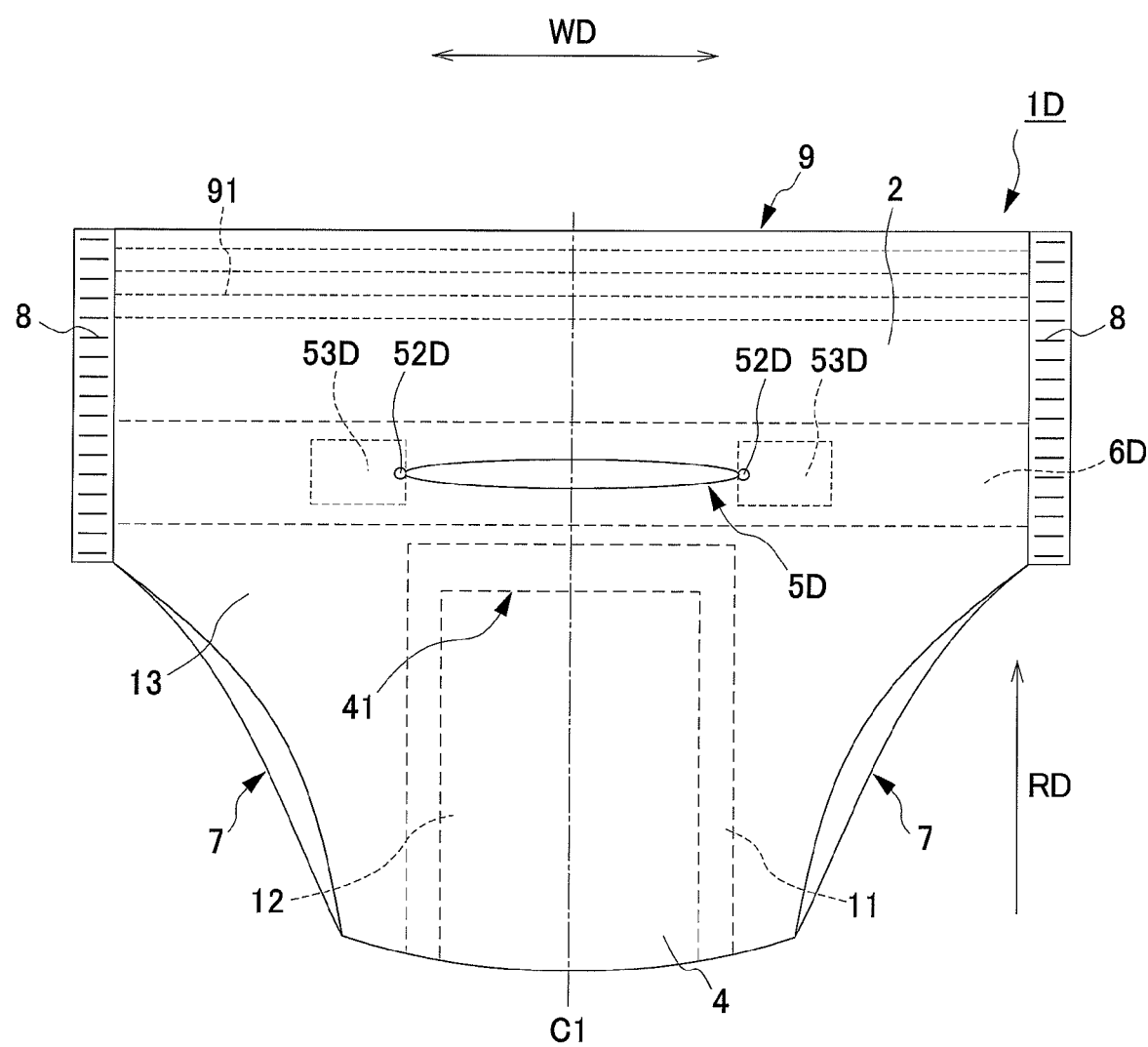
FIG. 20 is a front view of a disposable diaper according to a third embodiment of the present invention.

FIG. 11 is a perspective view showing a state in which the overlapping opening is opened. FIG. 12 is a perspective view showing a state in which the disposable diaper according to another example of the first embodiment is put on. FIG. 13 is a perspective view showing a state in which the overlapping opening of FIG. 12 is opened. FIG. 14 is a perspective exploded assembly drawing in the flattened state of a disposable diaper according to a second embodiment of the present invention. FIG. 15A is a front view of the disposable diaper of the second embodiment. FIG. 15B is a cross-sectional view taken along the line Y-Y in FIG. 15A. FIG. 16A is a perspective view showing a masking sheet as an auxiliary sheet. FIGS. 16B and 16C are perspective views showing other examples of the masking sheet, respectively. FIG. 17A is an exploded perspective view of a masking sheet where an absorptive member is arranged. FIG. 17B is a cross-sectional view taken along the line Z-Z of FIG. 17A. FIG. 18A is a front view showing a connection state of the masking sheet. FIG. 18B is a front view showing another connection state of the masking sheet. FIG. 19A is a cross-sectional view showing a connection state of the masking sheet. FIG. 19B is a cross-sectional view showing another connection state of the masking sheet. FIG. 20 is a front view of a disposable diaper according to a third embodiment of the present invention.

1. First Embodiment

1-1. General Configuration

The disposable diaper of the present invention is described with respect to a pants-type disposable diaper 1 in the first embodiment. As shown in FIGS. 1 to 2B, the disposable diaper 1 includes a chassis 13, a liquid permeable top sheet 11, a liquid impermeable back sheet 14 and a liquid retentive absorbent body 12. The chassis 13 forms the outline of the disposable diaper 1, and configures a front body 2, a rear body 3 and a crotch part 4. The liquid permeable top sheet 11 is disposed on the skin-contacting side of the chassis 13, and has a substantially elongated shape forming a top layer. The liquid impermeable back sheet 14 is disposed on the skin-non-contacting side of the chassis 13 as one side of the top sheet 11, and has a substantially elongated shape forming a back layer. The liquid retentive absorbent body 12 is disposed between the top sheet 11 and the chassis 13, and has a substantially elongated shape forming an absorbent layer.

The chassis 13 has a first chassis 13A forming a part of the front body 2, the rear body 3 and the crotch part 4, and a second chassis 13B forming a part of the front body 2 and has a rectangular shape. When worn, the first chassis 13A and the second chassis 13B are overlapped in part of the first and second chassis 13A and 13B in the front body 2, and connected to each other at a pair of connecting parts 21 disposed in an overlapping allowance. Specifically, the second chassis 13B is arranged at an end located in a longitudinal direction of the first chassis 13A, the end corresponding to the front body 2 during wearing, so that one side in the longitudinal direction of the second chassis 13B can be overlapped in the width direction of the end. The overlapping allowance has the connecting parts 21 at positions separated from each other across a center line C1 extending in a longitudinal direction (LD) of the disposable diaper 1, and dividing a width direction (WD) thereof into two parts. The first and second chassis 13A and 13B are connected to each other at the connecting parts 21. A non-contacting portion 22, disposed between the connecting parts 21, is intended for forming an overlapping opening 5. When the wearer pulls the first chassis 13A of the overlapping opening 5 as the non-connecting part 22, toward an inside leg direction (LGD), the opening can be expanded in the inside leg direction (LGD), thereby obtaining an opening of large enough to draw out the sex organ.

The first and second chassis 13A and 13B (the chassis 13) may be formed by a sheet member, or alternatively formed by stacking a plurality of sheet members one upon another. In the present embodiment, the disposable diaper 1 has a configuration in which the chassis 13 has the front body 2, the rear body 3 and the crotch part 4, and the top sheet 11, the absorbent body 12 and the back sheet 14 are arranged at predetermined positions of the chassis 13, respectively. The present invention is not limited to this configuration. For example, the chassis 13 may have the front body 2 and the rear body 3, and the crotch part 4 having the top sheet 11, the absorbent body 12 and the back sheet 14 may be independently connected to the chassis 13. In this case, the back sheet 14 in the crotch part 4 and the chassis 13 may be connected to each other. Alternatively, the back sheet 14 may also function as the chassis 13.

The top sheet 11 and the absorbent body 12 extend, on the skin-contacting side of the chassis 13, from the front body 2 through the crotch part 4 to the rear body 3 of the chassis 13. The back sheet 14 extends, on the skin-noncontacting side of the chassis 13, from the front body 2 through the crotch part 4 to the rear body 3 of the chassis 13. With this configuration, the excreta such as urine discharged from the wearer's excretory organ is passed through the liquid permeable region of the top sheet 11, and then absorbed by the absorbent body 12, whereas the back sheet 14 disposed on the skin-noncontacting side is liquid impermeable and hence the excreta such as urine is not passed through the skin-noncontacting side, and absorbed and held by the absorbent body 12, thereby preventing leakage to the outside.

The substantially elongated absorbent body 12 includes, for example, substantially rectangular ones having a longitudinal direction and a transverse direction, or alternatively, those in which a part of the sides extending in the longitudinal direction (LD) of the disposable diaper 1 is recessed toward the center line C1, or alternatively swelled in the opposite direction of the center line C1.

The front body 2 and the rear body 3 include, for example, those which extend in the width direction (WD) of the disposable diaper 1, and can be divided by a center line C2 dividing the longitudinal direction (LD) thereof into two parts.

FIG. 2A shows the disposable diaper 1 formed in a pants-type. As shown in FIG. 2A, the disposable diaper 1 of the present embodiment can be formed in the pants-type by connecting, at side seal parts 8 and 8, the front body 2 and the rear body 3 of the chassis 13 by employing an ultrasonic seal, etc. That is, the pants-type disposable diaper 1 is made up of the front body 2 positioned on the wearer's abdomen when worn, the rear body 3 positioned on the wearer's back when worn, and the crotch part 4 positioned in the vicinity of the wearer's crotch. The disposable diaper 1 also has, due to the formation in the pants-type, a waist opening 9 positioned at the wearer's waist when worn, and a pair of leg openings 7 and 7 positioned at the wearer's legs, respectively. As another connecting method at the side seal parts 8 and 8, hot sealing or a hot melt adhesive may be used to make the connection.

In the present embodiment, the pants-type disposable diaper 1, which can be formed in the pants-type having the waist opening 9 and the pair of leg openings 7 and 7 by connecting the front body 2 and the rear body 3 at the predetermined side seal parts 8 and 8, is described by way of example and without limitation. The present invention is also applicable to other uses, for example, as shown in FIG. 3B, as an expansion type disposable diaper 1A, which can be put on by engaging the front body 2 and the rear body 3 with an engaging member 8A, etc. Alternatively, an engaging member such as a surface fastener used in the expansion-type disposable diaper 1A may be disposed at the predetermined side seal parts 8 and 8 in the front body 2 and the rear body 3 of the pants-type disposable diaper. This provides a disposable diaper of a pants-type that can be expanded and reengaged by easy release and engagement.

Although in the present embodiment, the back sheet 14 is disposed on the skin-noncontacting side of the chassis 13, for example, the back sheet 14 may be disposed between the absorbent body 12 and the chassis 13. Alternatively, when the chassis 13 is made up of a plurality of stacked chassis members, the back sheet 14 may be disposed between the individual sheet members.

Furthermore, in the present invention, a leak preventing wall, a so-called solid gather (not shown), which can be formed by using an elastic member and a leak preventing sheet, may be arranged along both ends in the width direction (WD) of the absorbent body 12 of the disposable diaper 1. For example, in the disposable diaper 1 of the present invention, the solid gather is attained by disposing the leak preventing sheet so as to extend from between the absorbent body 12 and the chassis 13 or the back sheet 14 in the width direction (WD) of the absorbent body 12, and arranging at least one elastic member at the end in the width direction (WD) of the leak preventing sheet, and then fixing the two with hot melt adhesive, etc. The leak preventing sheet may remain extended in the width direction (WD) of the absorbent body 12. Alternatively, the leak preventing sheet may be folded back in the central direction in the width direction (WD) of the absorbent body 12, so that the folded-back part can be arranged on the skin-contacting side of the absorbent body 12.

As shown in FIGS. 4A and 4B, an elastic sheet having elasticity, such as an elastic non-woven fabric or an elastic film, is arranged on the front body 2 and the rear body 3 of the chassis 13 in the disposable diaper 1. This imparts tensibility or elasticity to the disposable diaper 1. In order to impart tensibility or elasticity to the disposable diaper 1, a thread-shaped elastic member may be arranged all or in part of each of the front body 2 and the rear body 3 of the chassis 13. Alternatively, an elastic sheet may be arranged in part of the front body 2 and in part of the rear body 3. Thus, the disposable diaper 1 has tensibility or elasticity by incorporating an elastic sheet or an elastic member into, for example, the waist as the entirety of the front body 2 and the rear body 3 of the chassis 13, or in part of the waist.

As a region having tensibility or elasticity owing to the elastic sheet, etc. may correspond to, for example, at least a part of an opening elastic region 55 formed along the waist of the chassis 13 in the shape of pants (underpants), while including substantially the center in the rear body 3 of the waist opening 9, and the vicinity of the crotch 4 located in the inside leg direction (LGD) of the overlapping opening 5. For example, the region may correspond to the overlapping opening 5 located in the inside leg direction (LGD) as a part of the opening elastic region 55 (for example, refer to FIGS. 7A and 7B). Alternatively, the region may correspond to an elastic boundary region 57 including all or in part of a boundary proximity having a connecting or an engaging position between the front body 2 and the rear body 3 (for example, refer to FIGS. 8A and 8B). Alternatively, the region may correspond to an elastic rear body region 56 including all or in part of the proximity of the rear body 3 as a part of the waist opening 9 (for example, refer to FIGS. 9A and 9B). The disposable diaper 1 may employ at least one of the opening elastic region 55, the elastic boundary region 57 and the elastic rear body region 56, or a combination thereof.

The disposable diaper 1 has, in a peripheral region of the waist opening 9, a so-called waist gather formed by disposing a thread-shaped elastic member 91 for elasticizing the waist opening 9. The waist gather enables suitable retention of the wearing position and the wearing condition of the pants-type disposable diaper 1 when worn. Alternatively, the disposable diaper 1 may have, in the peripheral regions of the leg openings 7 and 7, so-called leg gathers formed by disposing thread-shaped elastic members (not shown) for elasticizing the portions along the leg openings 7 and 7, respectively. For example, the leg gathers enable leak prevention owing to proper fastening of the waist during wearing. The elastic member 91 may be in the shape of a thread or strip. Furthermore, as the elastic member 91, it is possible to use an elastic sheet having elasticity such as an elastic non-woven fabric (for example, a non-woven fabric made of a mixed fabric of polyurethane and polypropylene), or an elastic film.

1-2. Overlapping Opening

As shown in FIG. 5, the overlapping opening 5 is disposed, for example, between the connecting parts 21 at positions separated from each other across the center line C1 of the disposable diaper 1. That is, the overlapping opening 5 is made up of the connecting parts 21 of the first and second chassis 13A and 13B, respectively, and a non-connecting part 22 disposed between the connecting parts 21.

As shown in FIG. 5, the overlapping opening 5 is preferably located at a waist region 23 in the front body 2. The waist region 23 includes the front body 2 and the rear body 3 of the disposable diaper 1, except for the crotch part 4. The overlapping opening 5 can be formed by overlapping the second chassis 13B with a part of the first chassis 13A, at a position apart from the outer edge on one side in the longitudinal direction (LD) of the absorbent body 12. Alternatively, the overlapping opening 5 may be formed by overlapping the second chassis 13B with a part of the first chassis 13A, at a position apart from the outer edge on one side in the width direction (WD) of the absorbent body 12. In cases where the outer edge of the absorbent body 12 is partially notched, the overlapping opening 5 may be formed by overlapping, for example, the second chassis 13B and the first chassis 13A at a position apart from the notched portion of the absorbent body 12 in a substantially parallel relation therewith.

Either one or both of the first chassis 13A and the second chassis 13B in the non-connecting part 22 of the disposable diaper 1 are entirely or partially provided with a plurality of thread-shaped elastic members 63 (for example, refer to FIGS. 6A and 6B). Thus, the presence of the thread-shaped elastic member 63 in the non-connecting part 22 can improve the skin-contacting properties with respect to the wearer's abdomen, thereby preventing the wearer's skin from being unintentionally exposed from the overlapping opening 5. For example, as shown in FIG. 6A, when the thread-shaped elastic member 63 is arranged in the overlapping opening 5 of the second chassis 13B, the non-connecting part 22 of the first chassis 13A can be pressed by the second chassis 13B. As shown in FIG. 6B, when the thread-shaped elastic member 63 is arranged in the overlapping opening 5 of the second chassis 13A, the non-connecting part 22 of the second chassis 13B can be pressed by the first chassis 13A. Although the elastic member 63 may be arranged in either the first chassis 13A or the second chassis 13B, it is preferably arranged in a sheet member corresponding to the skin-noncontacting side. As the elastic member 63, a strip-shaped elastic member such as an elastic non-woven fabric or an elastic film may be used.

The overlapping opening 5 in the non-connecting part 22 may connect in part of the first and second chassis 13A, and 13B under a weak connecting condition permitting easy detachment. The overlapping opening 5 as the non-connecting part 22 may be connected in the shape of a circle, an ellipse or a polygon, at predetermined spacing. That is, in the overlapping opening 5, the non-connecting part 22 may be entirely unconnected, or may be connected by a connecting means of a degree that a part thereof can be swtached easily.

1-3. Reinforcing Sheet

As shown in FIG. 1, a pair of reinforcing sheets 53 as reinforcing members is disposed at both ends of the overlapping opening 5 of the disposable diaper 1, respectively. The pair of reinforcing sheets 53 is shaped substantially in a rectangle, which is disposed between the first and second chassis 13A and 13B, and connected through the connecting part 21 to the chassis 13A and 13B.

As the reinforcing sheets 53, a member such as a nonwoven fabric or a film can be used which has, for example, a tearing strength of at least 5N (measuring method: A-1 method (single tang method) JIS L 1906) in both width direction and longitudinal direction. The reinforcing sheets 53 are connected to the first and second chassis 13A and 13B at both ends of the overlapping opening 5, respectively, by hot melt adhesive, hot seal, ultrasonic seal or the like. When the first and second chassis 13A and 13B as the chassis 13 are formed by a plurality of sheet members or the like, the reinforcing sheets 53 may be disposed between the sheet members in either the first chassis 13A or the second chassis 13B, so as to be connected or fastened from both surfaces of the sheet members. The present embodiment employs the substantially rectangular reinforcing sheets 53 by way of example and without limitation. It is possible to employ various shapes such as a circle, an ellipse and a polygon.

1-4. Hole Parts

As shown in FIG. 1, hole parts 52 are disposed at both ends of the connecting parts 21 in the overlapping opening 5, respectively. Specifically, the hole parts 52 are disposed at the corners located in a raised direction (RD) in the connecting parts 21 of the sheet members arranged on the skin-contacting side in either the first chassis 13A or the second chassis 13B. The hole parts 52 are for improving tear resistance strength and are able to disperse the tearing stress exerted on the connecting parts 21, for example, when the wearer opens the overlapping opening 5. Specifically, in the presence of the hole parts 52, instead of a point, the curved surfaces of the hole parts 52 can receive the tearing stress generated at the ends of the connecting parts 21 of the first and second chassis 13A and 13B. Thus, the tear resistance strength can be improved more than in the absence of the hole parts 52. The hole parts 52 may be in the shape of a circle, an ellipse or a polygon.

1-5. Opening Auxiliary Member

In the disposable diaper 1 of the present invention, a grip portion (not shown) as an opening auxiliary member may be disposed, for example, at the overlapping opening 5 located at the crotch part 4 or the waist opening 9. As the grip portion, a string-like or a strip-like base sheet may be connected to the front body 2 on the first chassis 13A or the second chassis 13B (the chassis 13). Alternatively, a tong-like projection may be disposed in the front body 2 in the first chassis 13A or the second chassis 13B (the chassis 13). By the presence of the grip portion as the opening auxiliary member, for example, the wearer can easily open the overlapping opening 5 by using the grip portion. Furthermore, even when a person who needs care wears the disposable diaper 1, a care person can easily open the overlapping opening 5 by pulling the grip portion. This facilitates care actions for the person needing care, such as for urination.

1-6. Guide Mark

In the disposable diaper 1 of the present invention, a guide mark (not shown) may be disposed, for example, in the vicinity of the overlapping opening 5. As a guide mark, a color may be applied to the crotch part 4 of the overlapping opening 5 or the waist opening 9 or the peripheral region of the overlapping opening 5. The color application enables the wearer to easily recognize the position of the overlapping opening 5, facilitating urination.

As the guide mark, a symbol such as an arrow or a character may be applied. By applying the symbol such as the arrow and the character, not only a wearer who urinates independently, but also the care person, etc. assisting in the urination action of the wearer can easily open the overlapping opening 5, without mistaking the position and the opening direction of the overlapping opening 5.

Alternatively, the guide mark may be attained by employing an indention process such as an embossing process, or by connecting a base sheet having indention to the crotch part 4 of the overlapping opening 5, or the waist opening 9 or the peripheral region of the overlapping opening 5. This enables the wearer to confirm the position of the overlapping opening 5 only by touching the periphery of the overlapping opening 5, thus facilitating in urination.

1-7. Manner to Use

The manner of use of the disposable diaper 1 in the first embodiment is described below.

As shown in FIG. 10, the disposable diaper 1 of the present embodiment is formed in the shape of pants (underpants), and can be put on and used by the wearer in the same manner as in usual underpants. At the time of urination, for example, the wearer widens the overlapping opening 5 by inserting a finger, etc. into the overlapping opening 5 as the non-connecting part 22 of the first and second chassis 13A and 13B, respectively, and then pulling the first chassis 13A at the overlapping opening 5 toward the inside leg direction (LGD). At this time, the tear of the overlapping opening 5 or the stripping of the first and second chassis 13A and 13B, respectively, can be prevented by the presence of the reinforcing sheets 53 on both ends of the overlapping opening 5.

When the disposable diaper 1 has a string-like opening auxiliary member (not shown) located in the inside leg direction (LGD) of the overlapping opening 5, the wearer may widen the overlapping opening 5 by gripping the opening auxiliary member or hooking it over a finger, etc. and pulling it toward the inside leg direction (LGD). On the other hand, when a guide mark (not shown), such as the application of a color or the arrangement of the non-woven fabric, etc. having an indentation is applied to the vicinity of the overlapping opening 5, such as the second chassis 13B located in the raised direction (RD) of the overlapping opening 5, or the first chassis 13A located in the inside leg direction (LGD) of the overlapping opening 5, it is easy for the wearer to recognize the position of the overlapping opening 5.

Subsequently, the wearer further pulls a part of the opened overlapping opening 5 toward the inside leg direction (LGD). As a result, a predetermined position in the chassis 13 (for example, refer to FIGS. 7B, 8B and 9B) extends in a direction in which the wearer pulls, as shown in FIG. 11. This ensures that the overlapping opening 5 has an opening large enough to enable the male sex organ to be drawn out. Therefore, the wearer can easily draw out the male sex organ. Here, the chassis 13 may be entirely extended. Alternatively, the opening elastic region 55, where substantially the center of the rear body 3 of the waist opening 9 and substantially the center of the front body 2 of the overlapping opening 5 are connected to each other along the outer periphery in the shape of the pants, may be entirely or partially extended as shown in FIG. 7A. By the entire or partial extension of the opening elastic region 55 in the chassis 13, the opening formed by the overlapping opening 5 can be extended toward the crotch part 4, namely in the direction in which the wearer pulls. This enables the overlapping opening 5 to ensure an opening through which the male sex organ can be drawn out.

The following can be exemplified as another elastic region of the chassis 13 where the overlapping opening 5 can form an opening large enough to enable the male sex organ to be drawn out. The first example is the elastic rear body region 56 that can be formed by applying a stretchable elastic member to the rear body 3 in the vicinity of the waist opening 9, as shown in FIG. 8A. By imparting elasticity to at least the elastic rear body region 56 in the chassis 13, the opening formed by the overlapping opening 5 can be extended toward the crotch part 4, namely the direction in which the wearer pulls, as shown in FIG. 8B. This enables the overlapping opening 5 to ensure an opening through which the male sex organ can be drawn out.

The second example is the elastic boundary region 57 that can be formed by applying a stretchable elastic member to the entirety or a part of the boundary proximity including the connecting or engaging position between the front body 2 and the rear body 3, as shown in FIG. 9A. By imparting elasticity to at least the elastic boundary region 57 in the chassis 13, the opening formed by the overlapping opening 5 can be extended toward the crotch part 4, namely the direction in which the wearer pulls, as shown in FIG. 9B. This enables the overlapping opening 5 to ensure an opening through which the male sex organ can be drawn out.

The elastic rear body region 56 and the elastic boundary region 57 may be stretchable in conjunction with the abovementioned waist gather (not shown). Alternatively, either the elastic rear body region 56 or the elastic boundary region 57 may be made stretchable. Although the present embodiment does not have the abovementioned leg gathers, thread-like elastic members may be disposed in the peripheral regions of the leg openings 7, respectively, or alternatively, strip-like elastic members such as elastic non-woven fabrics or elastic films may be disposed in all or part of the peripheries of the leg openings 7, respectively.

Thus, it is easy for the wearer to draw out the male sex organ, even when wearing the disposable diaper 1, and it is therefore possible to draw out the male sex organ one-handed. This enables urination without requiring removal of the disposable diaper 1. Additionally, owing to the characteristic features in that the opening direction (the direction in which the wear pulls) in the overlapping opening 5 is directed to the crotch part 4, and that the overlapping opening 5 has the substantially elongated shape extending in the width direction (WD) of the disposable diaper 1, the overlapping opening 5 can be easily opened toward the crotch part 4, whether the wearer is right-handed or left-handed.

Furthermore, owing to the characteristic feature that the first and second chassis 13A and 13B (the chassis 13), respectively, having elasticity are arranged on the skin-contacting side or the skin-noncontacting side of the overlapping opening 5, the first and second chassis 13A and 13B (the chassis 13) can be brought into contact with the wearer's abdomen during normal use and after urination. This prevents unintentional exposure of the wearer's skin and the male sex organ. Additionally, the elastic members arranged in the first and second chassis 13A and 13B (the chassis 13), respectively, enable improvement in fit feeling of the disposable diaper 1.

1-8. Other Examples of First Embodiment

A disposable diaper 1B according to another example of the first embodiment of the present invention is described with reference to FIGS. 12 and 13. As shown in FIGS. 12 and 13, the disposable diaper 1B is different from the first embodiment in that the elastic boundary region 57 is provided as a stretchable region of the chassis 13 consisting of the first and second chassis 13A and 13B, respectively.

The elastic boundary region 57 can be formed by arranging a thread-like elastic member or a strip-like elastic member, such as an elastic non-woven fabric or an elastic film, in the boundary proximity including the connecting or engaging position between the front body 2 and the rear body 3 of the disposable diaper 1B. Thus, in the disposable diaper 1B, the tensile stress of the front body 2 including areas located in the raised direction (RD) and in the inside leg direction (LGD) of the overlapping opening 5B is smaller than the tensile stress of other areas. Hence, the elastic boundary region becomes stretchable when the wearer pulls the opening of the overlapping opening 5B.

Leg gathers formed by arranging thread-like elastic members or strip-like elastic members such as elastic non-woven fabrics or elastic films may be disposed in all or in part of the peripheries of the leg openings 7, respectively. Alternatively, no leg gather may be disposed there. Similarly, the so-called waist gather may be disposed in all or in part of the peripheries of the abdomen opening 9. Alternatively, no waist gather may be disposed there.

Thus, the disposable diaper 1B is arranged so that the tensile stress of the front body 2 including the areas located in the raised direction (RD) and in the inside leg direction (LGD) of the overlapping opening 5B is smaller than the tensile stress of other areas. For example, it may be arranged so that no elastic member is applied to, or alternatively a less stretchable elastic member is applied to the areas located in the raised direction (RD) and in the inside leg direction (LGD) of the overlapping opening 5B. Therefore, in the proximity of the overlapping opening 5B of the disposable diaper 1B, the elastic member or the like generates no shrinkage (gather) in the width direction (WD), or less shrinkage (gather) than in other areas. This enables the length of the overlapping opening 5 to be retained almost at the maximum. Additionally, at least a part of the elastic boundary region 57 can be extended by elasticity, so that the overlapping opening 5 can be easily extended in the inside leg direction (LGD), and ensure an opening having a predetermined dimension.

2. Second Embodiment

A disposable diaper 1C according to a second embodiment of the present invention is described with reference to FIGS. 14 to 19B. Unless otherwise stated, the second embodiment is identical to the first embodiment, and the same references have been used as in the first embodiment for similar parts.

As shown in FIGS. 14 to 15B, the disposable diaper 1C is different from the disposable diapers 1, 1A and 1B in that the chassis 13 is formed by a sheet member, and an openable slit part 5C is formed at a predetermined position in the front body 2 when worn. The following description of the disposable diaper 1C of the second embodiment is made mainly of the different points from the first embodiment.

As shown in FIG. 14, the slit part 5C extends in the longitudinal direction (LD) of the disposable diaper 1C, and is formed along cutting guide line connecting points separated from each other across a center line C1 that divides the width direction (WD) into two parts. Specifically, as shown in FIG. 15A, the slit part 5C can be formed by alternately disposing a cutting portion 5a and a non-cutting portion 5b along the cutting guide line. A cleavage part 51C, which causes the slit part 5C to be in the pre-cleavage state by cutting a part of the slit part 5C to a predetermined length, is disposed substantially in the center of the slit part 5C. Hole parts 52C are disposed at both ends of the slit part 5C, respectively. Reinforcing sheets 53C, as reinforcing members, are arranged in the vicinity of both ends of the slit part 5C including the hole parts 52C, respectively. The slit part 5C is covered with a masking sheet 6 as an auxiliary sheet.

2-1. Slit Part

As shown in FIG. 14 and FIG. 15A, the slit part 5C is attained by intermittently and sequentially forming the cutting portion 5a, such as slit-like cut lines or openings, along the cutting guide line connecting points separated from each other across the center line C1 of the disposable diaper 1C. In other words, the slit part 5C is a scored region in which the cutting portion 5a and the non-cutting portions 5b are continuously formed. By breaking the respective cutting portions 5b in the slit part 5C, the wearer opens and uses the slit part 5C as an opening, through which the male sex organ is drawn out.

As a first example, the slit part 5C may be formed linearly in the width direction (WD) orthogonal to the center line C1, or formed so as to make with the center line C1 a predetermined angle. As a second example, the slit part 5C may be formed in a predetermined shape such as a curved waveform, a polygon or a circle. As a third example, the slit part 5C may be disposed in a region formed in a part (the inside) of the absorbent body 12. As a fourth example, the absorbent body 12 may be divided into a plurality of segments, and a region for the slit part 5C may be formed between the segments.

The slit part 5C is formed at a position apart from the outer edge of the absorbent body 12 in the front body 2. For example, the slit part 5C may be disposed at a position apart from the outer edge in the longitudinal direction (LD) of the absorbent body 12, or alternatively at a position apart from the outer edge in the width direction (WD) of the absorbent body 12.

2-2. Cleavage Part

The cleavage part 51 that is a partially pre-cleaved portion of the slit part 5C is disposed substantially in the center of the slit part 5C. For example, the cleavage part 51 may have a dimension large enough to hook the wearer's finger when opening the slit part 5C. Specifically, the cleavage part 51 may have the same slit-shape as the cutting portion 5a, or alternatively a rectangular or polygon shape, or a shape having curved portions, such as an ellipse. When the cutting portion 5a is formed substantially at the center of the cutting part 5C, the cutting portion 5a may serve as the cleavage part 51. The presence of the cleavage part 51 enables the wearer to insert a finger or the like into the slit part 5C, from which the slit part 5C can be opened easily.

When a part of the slit part 5C, namely the portion corresponding to the cleavage 51, is formed so as to protrude toward the skin-noncontacting side, the protruded portion of the cleavage 51 can be grasped, instead of insertion of the finger into the cleavage 51. It is easy to open the slit part 5C. Preferably, a material having high rigidity is disposed at the portion corresponding to the cleavage part 51, namely the protruded portion.

2-3. Hole Parts

Hole parts 52C are disposed at both ends of the slit part 5C, respectively. The hole parts 52C are for improving tear resistance strength, and are able to disperse the tearing stress exerted on both ends of the slit part 5C, for example, when the wearer opens the overlapping opening 5. Specifically, in the presence of the hole parts 52C, instead of a point, the curved surfaces of the hole parts 52C can receive the tearing stress generated at the ends of the slit part 5C. Therefore, the tear resistance strength can be improved more than the case in the absence of the hole parts 52C.

Instead of the hole parts 52C, the ends of the slit part 5C may have curved portions (not shown), which are curved in a different direction from the direction of extension of the slit part 5C. This is because the curved portions can disperse tearing stress. The curved portions may be made up of curves. A line may be bent to form the curved portions.

2-4. Reinforcing Sheets

A pair of reinforcing sheets 53C formed substantially in a rectangle are disposed at both ends of the slit part 5C in the disposable diaper 1C, respectively. It is preferable to precut the reinforcing sheets 53C positioned at locations where the reinforcing sheets 53C at both ends of the slip part 5C are overlapped with the slit part 5C. This is because when the reinforcing sheets 53C are disposed at the locations of the slit part 5C, it is difficult to cut the inseparable portion 5b of the slit part 5C.

The material composing the reinforcing sheets 53C may be the same as in first embodiment.

2-5. Masking Sheet

A masking sheet 6 is connected to the skin-contacting side or the skin-noncontacting side of the chassis 13, so as to cover the slit part 5C. Therefore, the masking sheet 6 may have a longitudinal length dimension long enough to cover the slit part 5C. For example, the longitudinal length thereof may be substantially the same as the length in the width direction (WD) of the disposable diaper 1C.

As shown in FIG. 16A, the masking sheet 6 can be formed by sandwiching a plurality of thread-shaped elastic members 63 between a pair of strip-shaped base sheets 61. Specifically, the masking sheet 6 can be formed by sandwiching the plurality of extended elastic members 63 between the base sheets 61 such as non-woven fabrics, and fixing each of the base sheets 61 with hot melt adhesive, etc. By releasing the tension of the elastic members 63 after the fixing, a so-called gather can be formed, enabling the masking sheet 6 to be extended the amount of the gather.

As shown in FIG. 16B, the masking sheet 6 may be formed by bonding a strip-shaped elastic member 64 and the base sheet 61. For example, the masking sheet 6 may be formed by sandwiching a stripe-shaped elastic member 64 between a pair of base sheets 61, and by bonding each of the base sheets 61. Alternatively, the masking sheet 6 may be formed by folding a base sheet 61, and by interposing elastic members 63 and 64 into spacing made by the folding. As a strip-shaped elastic member, a base sheet such as an elastic non-woven fiber member may be used to serve as the masking sheet 6.

As shown in FIG. 16C, the masking sheet 6 may be formed by sticking a liquid impermeable sheet 65, such as polyethylene (PE) or polypropylene (PP) film, to a base sheet 61 such as a non-woven fabric. When the base sheet 61 is made up of a plurality of stacked sheets, the liquid impermeable sheet 65 may be sandwiched between the base sheets 61.

As shown in FIGS. 17A and 17B, an absorber 67 composed of an absorptive material, and a liquid impermeable sheet 66 covering the absorber 67, may be arranged entirely or partially on the skin-contacting side or the skin-noncontacting side of the masking sheet 6. By the absorber 67 located entirely or partially of the masking sheet 6, even if a urine leak occurs during the course of drawing out the male sex organ, the absorber 67 of the masking sheet 6 can absorb the leaked urine, thereby preventing the clothes from being stained.

As shown in FIGS. 18A and 18B, the masking sheet 6 is connected through a connecting part 68 to the chassis 13 so as to cover the entirety of the slit part 5C. For example, as shown in FIG. 18A, the masking sheet 6 may be connected to the chassis 13 throughout the entirety of the front body 2 located in the inside leg direction (LGD) of the slit part 5C, and the front body 2 on both ends located in the longitudinal direction of the masking sheet 6. For example, as shown in FIG. 18B, the masking sheet may be connected to the chassis 13 throughout the entirety of the front body 2 located in the raised direction (RD) of the slit part 5C and the front body 2 on both ends located in the longitudinal direction of the masking sheet 6.

As shown in FIG. 19A, the masking sheet 6 may be connected to the chassis 13 at a connecting part 68 located in the raised direction (RD) of the slit part 5C on the skin-contacting side or the skin-noncontacting side of the chassis 13. Alternatively, the masking sheet 6 may be connected to the chassis 13 at a connecting part 68 located in the inside leg direction (LGD) of the slit part 5C on the skin-contacting side or the skin-noncontacting side of the chassis 13.

When the masking sheet 6 is connected to the slit part 5C located in the raised direction (RD) (the waist opening 9) on the skin-contacting side of the chassis 13, an elastic member is preferably disposed in at least part of the area located in the raised direction (RD) (the crotch part 4) of the slit part 5C.

When the masking sheet 6 is connected to the slit part 5C located in the inside leg direction (LGD) (the crotch part 4) on the skin-contacting side of the chassis 13, an elastic member is preferably disposed in at least part of the area located in the raised direction (RD) (the waist opening 9) of the slit part 5C.

Thus, by the elastic force of the elastic member 63, the masking sheet 6 is brought into contact with the wearer's abdomen so as to prevent the wearer's skin from being exposed when worn. On the other hand, when the wearer opens the slit part 5C, the masking sheet 6 follows the opening state of the slit part 5C and becomes extensible the amount of the gather. When the masking sheet is disposed on the skin-noncontacting side of the slit part 5C, it is possible to bring the chassis 13 located at the slit part 5C into contact with the wearer's skin, etc., and also prevent the wearer's skin, etc. from being exposed. When the masking sheet is disposed on the skin-contacting side of the slit part 5C, it is possible to pull the chassis 13 located at the slit part 5C toward the wearer's skin, etc., and also prevent the wearer's skin, etc. from being exposed.

2-6. Another Example of Second Embodiment

As an openable part of the disposable diaper 1C in the second embodiment, a light wall portion shaped in an easy-to-cut thin-walled state may be disposed in the chassis 13.

The thin-walled portion can be obtained by pressing such as embossing. Alternatively, the weight of the corresponding portion may be reduced to form the thin-walled portion.

3. Third Embodiment

A disposable diaper 1D according to a third embodiment of the invention is described with reference to FIG. 20. Unless otherwise stated, the third embodiment is identical to the first embodiment, and the same references have been used as in the first embodiment for similar parts.

As shown in FIG. 20, the disposable diaper 1D is different from the disposable diapers 1, 1A and 1B in that the chassis 13 is formed by a sheet member, and an opening 5D is formed at a predetermined position in the front body 2 when worn. The opening 5D is elongated so as to extend in the width direction (WD) of the disposable diaper 1D, and is usually covered with a masking sheet 6 as an auxiliary sheet. The following description of the disposable diaper 1D of the third embodiment is made mainly of the different points from the first embodiment.

3-1. Opening

As shown in FIG. 20, the opening 5D extends in the longitudinal direction (LD) of the disposable diaper 1D, and is composed of a line or a pattern, or a combination thereof, which passes through points separated from each other across a center line C1 that divides the width direction (WD) into two parts. For example, the opening 5D has an ellipse composed substantially of a curve. Alternatively, the opening 5D may be formed by a combination of a slit-shaped opening and a substantially ellipse-shaped opening. When the opening 5D is composed of a line connecting points separated from each other across the center line C1, or both ends thereof are formed so as to make an acute angle with respect to the horizontal, hole parts 52D, or reinforcing sheets 53D for improving tear resistance strength, are preferably disposed at both ends of the opening 5D, respectively. This enables prevention of breakage at both ends of the opening 5D when the wearer pulls the opening 5D.

The opening 5D may be disposed in a region formed in a part (the inside) of the absorbent body 12. Alternatively, the absorbent body 12 may be divided into a plurality of segments, and a region for the opening 5D may be formed between the segments.

The opening 5D is formed at a position apart from the outer edge of the absorbent body 12 in the front body. In other words, the opening 5D may be disposed at a position apart from the outer edge in the width direction (WD) or the longitudinal direction (LD) of the absorbent body 12. When the absorbent body 12 is partially notched, the opening 5D may be disposed at a position separated substantially in parallel to the notched portion of the absorbent body 12. That is, the opening 5D may be extend in the longitudinal direction (LD) of the disposable diaper 1D, and curved obliquely or formed linearly so as to have a predetermined angle with respect to substantially the center line C1 that divides the width direction (WD) into two parts. The opening 5D may be in the shape of a polygon or substantially a circle.

3-2. Hole Parts

Hole parts 52D are provided at both ends of the opening 5D, respectively. The hole parts 52D may have the same construction as those in the disposable diaper 1C of the second embodiment. The hole parts 52D can be identical to those in the disposable diaper 1C of the second embodiment in position, dimension, and range.

3-3. Reinforcing Sheets

A pair of reinforcing sheets 53D as reinforcing members are disposed at both ends of the opening 5D, respectively (refer to FIG. 20). The reinforcing sheets 53D may be identical to those in the disposable diaper 1C. The reinforcing sheets 53D can be identical to those in the disposable diaper 1C of the second embodiment in position, dimension and range.

3-4. Masking Sheet

A masking sheet 6D is disposed so as to cover the opening 5D. The masking sheet 6D may be identical to that in the disposable diaper 1C. The masking sheet 6D may be identical to that in the disposable diaper 1C of the second embodiment in position, dimension, and range.

While the preferred embodiments of the present invention have been described and illustrated above, it is to be understood that they are exemplary of the invention and are not to be considered to be limiting. Additions, omissions, substitutions, and other modifications can be made thereto without departing from the spirit or scope of the present invention. Accordingly, the invention is not to be considered to be limited by the foregoing description and is only limited by the scope of the appended claims.

What is claimed is:

1. A disposable diaper having an openable section for facilitating urination, the disposable diaper comprising:
   a chassis defining at least a front body, a rear body and a crotch part located between the front body and the rear body;
   a liquid permeable top sheet and a liquid impermeable back sheet on opposite sides and covering at least part of the chassis;
   a liquid retentive absorber disposed between the top sheet and the back sheet and extending from the front body through the crotch part to the rear body of the chassis; and
   wherein the front body of the chassis has
      the openable section including a tearable line that extends in a width direction of the disposable diaper;
      a pair of reinforcing sheets disposed at both ends of the openable section, respectively, wherein the openable section is pre-cut in each of the reinforcing sheets which overlap the tearable line;
      an elastic auxiliary sheet covering the openable section and located on a skin-contactable side when the disposable diaper is worn by a wearer, wherein the auxiliary sheet includes (i) a pair of base sheets extending across an entire width of the front body, and (ii) a plurality of elastic members, said auxiliary sheet being formed by sandwiching the elastic members between said base sheet and fixing the elastic members to each of the base sheets with adhesive, and by releasing a tension of the elastic members after the fixing, and
   the auxiliary sheet further has a connecting part where the auxiliary sheet is connected to the chassis, said connecting part extending in the width direction without covering the openable section
   wherein said openable section, when torn, defines an opening and said elastic auxiliary sheet renders the opening widenable in response to an external force applied to the chassis around the opening and returns the opening to an initial form upon removal of the external force.

2. The disposable diaper according to claim 1, further comprising holes disposed at two ends of the tearable line, respectively.

3. The disposable diaper according to claim 1, wherein each said reinforcing sheet comprises a non-woven fabric having a tearing strength of at least 5N in the width direction and in the longitudinal direction, and is bonded to the chassis by at least one of hot melt adhesive, hot seal or ultrasonic seal.

4. The disposable diaper according to claim 1, wherein each said reinforcing sheet comprises a film member having a tearing strength of at least 5N in the width direction and in the longitudinal direction, and is bonded to the chassis by at least one of hot melt adhesive, hot seal or ultrasonic seal.

5. The disposable diaper according to claim 1, wherein the tearable line comprises a plurality of perforations intermittently arranged in the width direction on the front body of the chassis, and at least a slit coincided with the tearable line and having a length large enough for receiving a finger for tearing of the tearable line.

6. The disposable diaper according to claim 5, wherein the slit is disposed substantially in a center of the openable section, and the plurality of perforations extend from the slit to both ends of the openable section along the width direction, respectively.

7. The disposable diaper according to claim 1, wherein the connecting part extends in the width direction along and below the tearable line.

8. A disposable diaper having an openable section for facilitating urination, said disposable diaper comprising:
   a chassis defining at least a front body, a rear body and a crotch part between the front body and the rear body;
   a liquid permeable top sheet and a liquid impermeable back sheet on opposite sides and covering at least part of the chassis;
   a liquid retentive absorber disposed between the top sheet and the back sheet, and extending from the front body through the crotch part to the rear body of the chassis; and
   an elastic region having an elastic member arranged in at least part of the chassis,
   wherein the front body of the chassis has the openable section including a tearable line that extends in a width direction of the disposable diaper; and a pair of reinforcing sheets disposed at both ends of the openable section, respectively, said openable section being pre-cut in each of the reinforcing sheets which overlap the tearable line, wherein said openable section, when torn, defines an opening and said elastic region renders the opening widenable in response to an external force applied to the chassis around the opening and returns the opening to an initial form upon removal of the external force.

9. The disposable diaper according to claim 8, further comprising holes disposed at two ends of the tearable line, respectively.

10. The disposable diaper according to claim 8, wherein each said reinforcing sheet comprises a film member having a tearing strength of at least 5N in the width direction and in the longitudinal direction, and is bonded to the chassis by at least one of hot melt adhesive, hot seal or ultrasonic seal.

11. The disposable diaper according to claim 8, wherein each said reinforcing sheet comprises a film member having a tearing strength of at least 5N in the width direction and in the longitudinal direction, and is bonded to the chassis by at least one of hot melt adhesive, hot seal or ultrasonic seal.

12. The disposable diaper according to claim 8, wherein the tearable line comprises a plurality of perforations intermittently arranged in the width direction on the front body of the chassis, and at least a slit coincided with the tearable line and having a length large enough for receiving a finger for tearing of the tearable line.

13. The disposable diaper according to claim 12, wherein the slit is disposed substantially in a center of the openable section, and the plurality of perforations extend from the slit to both ends of the openable section along the width direction, respectively.

\* \* \* \* \*